(12) United States Patent
Baril et al.

(10) Patent No.: US 11,801,052 B2
(45) Date of Patent: Oct. 31, 2023

(54) ASSEMBLIES FOR SURGICAL STAPLING INSTRUMENTS

(71) Applicant: Covidien LP, Mansfield, MA (US)

(72) Inventors: Jacob C. Baril, Norwalk, CT (US); Roanit A. Fernandes, Hyderabad (IN); Thomas Casasanta, Jr, Southington, CT (US); Christopher M. Meehan, Milford, CT (US); Saumya Banerjee, Collinsville, CT (US); Justin J. Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 82 days.

(21) Appl. No.: 17/460,469

(22) Filed: Aug. 30, 2021

(65) Prior Publication Data

US 2023/0066004 A1 Mar. 2, 2023

(51) Int. Cl.
*A61B 17/072* (2006.01)

(52) U.S. Cl.
CPC .... *A61B 17/07292* (2013.01); *A61B 17/07207* (2013.01); *A61B 2017/07264* (2013.01); *A61B 2017/07271* (2013.01); *A61B 2017/07285* (2013.01)

(58) Field of Classification Search
CPC ......... A61B 17/07292; A61B 17/07207; A61B 2017/07264; A61B 2017/07271; A61B 2017/07285
USPC ........................................... 227/175.1-182.1
See application file for complete search history.

(56) References Cited

U.S. PATENT DOCUMENTS

| 3,054,406 | A | 9/1962 | Usher |
| 3,124,136 | A | 3/1964 | Usher |
| 3,364,200 | A | 1/1968 | Ashton et al. |
| 3,499,591 | A | 3/1970 | Green |

(Continued)

FOREIGN PATENT DOCUMENTS

| CA | 2282761 A1 | 9/1998 |
| DE | 1602563 U | 3/1950 |

(Continued)

OTHER PUBLICATIONS

Australian Examination Report No. 1 corresponding to AU 2011250822 dated May 18, 2015.

(Continued)

*Primary Examiner* — Dariush Seif
(74) *Attorney, Agent, or Firm* — Carter, DeLuca & Farrell LLP

(57) ABSTRACT

A loading assembly includes a cartridge having a cartridge body with rows of staple pockets. A carrier includes a platform adapted to releasably retain the cartridge. A shell is laterally spaced from the platform and flexibly coupled thereto. The arm extends through the shell at an acute angle and the shell has a passage that is configured to receive a jaw member of a surgical stapling instrument therethrough. A surgical buttress has a distal region with a first orifice and a cutout and a proximal region with a second orifice. The first orifice is attachable to a peg located in a distal region of the shell and the second orifice is attachable to a post located in a distal region of the cartridge such that a portion of the surgical buttress extends through the passage of the shell. The cutout is configured to receive an arm of the platform therethrough.

16 Claims, 14 Drawing Sheets

(56) References Cited

U.S. PATENT DOCUMENTS

| | | |
|---|---|---|
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A * | 5/1999 | Frater et al. ..... A61B 17/07207 606/148 |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balázs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B1 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |

(56) References Cited

U.S. PATENT DOCUMENTS

| | | |
|---|---|---|
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV et al. |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2* | 2/2010 | Prommersberger . A61B 17/072 227/176.1 |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2* | 12/2010 | Marczyk et al. ..... A61B 17/105 227/181.1 |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2* | 9/2011 | Aranyi et al. .... A61B 17/07207 227/176.1 |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2* | 10/2011 | Stopek ..................... 227/176.1 |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2* | 11/2012 | Aranyi ............ A61B 17/07292 227/176.1 |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |

(56) References Cited

U.S. PATENT DOCUMENTS

| | | | |
|---|---|---|---|
| 8,584,920 B2 | 11/2013 | Hodgkinson |
| 8,590,762 B2 | 11/2013 | Hess et al. |
| 8,616,430 B2 | 12/2013 | (Prommersberger) Stopek |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (née Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (née Prommersberger) Stopek |
| 10,098,639 B2 | 10/2018 | Hodgkinson |
| 10,111,659 B2 | 10/2018 | Racenet et al. |
| 10,154,840 B2 | 12/2018 | Viola et al. |
| 10,881,395 B2* | 1/2021 | Merchant et al. ....... A61B 17/07292 |
| 2002/0091397 A1 | 7/2002 | Chen |
| 2002/0151911 A1 | 10/2002 | Gabbay |
| 2002/0165563 A1* | 11/2002 | Grant et al. ......... A61B 17/072 |
| | | 606/151 |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson, IV et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0004407 A1* | 1/2006 | Hiles et al. ......... A61B 17/0643 |
| | | 606/215 |
| 2006/0008505 A1 | 1/2006 | Brandon |
| 2006/0025816 A1* | 2/2006 | Shelton, IV et al. ....................... A61B 17/07207 |
| | | 606/215 |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1* | 10/2007 | Pace-Floridia et al. ................... A61L 31/048 |
| | | 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |

(56) References Cited

U.S. PATENT DOCUMENTS

| | | |
|---|---|---|
| 2008/0220047 A1 | 9/2008 | Sawhney et al. |
| 2008/0290134 A1 | 11/2008 | Bettuchi et al. |
| 2008/0308608 A1* | 12/2008 | Prommersberger . A61B 17/105 227/176.1 |
| 2009/0001121 A1 | 1/2009 | Hess et al. |
| 2009/0001122 A1* | 1/2009 | Prommersberger et al. ............... A61B 17/07292 227/176.1 |
| 2009/0001130 A1 | 1/2009 | Hess et al. |
| 2009/0031842 A1 | 2/2009 | Kawai et al. |
| 2009/0134200 A1* | 5/2009 | Tarinelli et al. . A61B 17/07207 227/176.1 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1* | 8/2009 | Huitema et al. . A61B 17/07207 227/176.1 |
| 2009/0218384 A1* | 9/2009 | Aranyi ............ A61B 17/07292 227/176.1 |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0065606 A1* | 3/2010 | Stopek ............... A61B 17/115 227/176.1 |
| 2010/0087840 A1 | 4/2010 | Ebersole et al. |
| 2010/0147921 A1* | 6/2010 | Olson ............... A61B 17/1155 227/175.1 |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1* | 9/2010 | Aranyi et al. .... A61B 17/07207 227/176.1 |
| 2010/0331859 A1 | 12/2010 | Omori |
| 2011/0034910 A1 | 2/2011 | Ross et al. |
| 2011/0087279 A1* | 4/2011 | Shah et al. ........ A61B 17/07207 606/219 |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0215132 A1* | 9/2011 | Aranyi et al. .... A61B 17/07207 227/176.1 |
| 2011/0215133 A1* | 9/2011 | Aranyi ............ A61B 17/07292 227/176.1 |
| 2011/0270235 A1* | 11/2011 | Olson et al. ..... A61B 17/07207 606/1 |
| 2011/0293690 A1 | 12/2011 | Griffin et al. |
| 2012/0080336 A1 | 4/2012 | Shelton, IV et al. |
| 2012/0125792 A1* | 5/2012 | Cassivi ........... A61B 17/07292 227/175.1 |
| 2012/0145767 A1* | 6/2012 | Shah et al. ....... A61B 17/07207 227/176.1 |
| 2012/0187179 A1* | 7/2012 | Gleiman ............ A61B 17/072 227/181.1 |
| 2012/0197272 A1 | 8/2012 | Oray et al. |
| 2012/0234900 A1* | 9/2012 | Swayze ........... A61B 17/07207 227/180.1 |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2012/0305626 A1* | 12/2012 | Stopek ................ A61B 17/068 227/176.1 |
| 2013/0062394 A1* | 3/2013 | Smith et al. ..... A61B 17/07292 227/176.1 |
| 2013/0105548 A1* | 5/2013 | Hodgkinson et al. ...................... A61B 17/07292 227/176.1 |
| 2013/0112731 A1* | 5/2013 | Hodgkinson ........ A61B 17/105 227/176.1 |
| 2013/0153634 A1* | 6/2013 | Carter et al. ....... A61B 17/1155 227/176.1 |
| 2013/0153636 A1 | 6/2013 | Shelton, IV et al. |
| 2013/0153641 A1* | 6/2013 | Shelton, IV et al. . A61B 17/068 227/180.1 |
| 2013/0193190 A1* | 8/2013 | Carter et al. ........ A61B 17/068 227/179.1 |
| 2013/0214030 A1* | 8/2013 | Aronhalt et al. ...... A61B 17/068 227/176.1 |
| 2013/0256380 A1 | 10/2013 | Schmid et al. |
| 2014/0048580 A1* | 2/2014 | Merchant et al. .... A61B 17/064 227/176.1 |
| 2014/0131418 A1* | 5/2014 | Kostrzewski .... A61B 17/07292 227/176.1 |
| 2014/0158742 A1* | 6/2014 | Stopek (nee Prommersberger) et al. ................... A61B 17/072 227/175.1 |
| 2014/0166721 A1* | 6/2014 | Stevenson et al. ........ 227/176.1 |
| 2014/0203061 A1* | 7/2014 | Hodgkinson .... A61B 17/07292 227/175.1 |
| 2014/0224686 A1* | 8/2014 | Aronhalt et al. ... A61B 17/0644 206/339 |
| 2014/0239047 A1 | 8/2014 | Hodgkinson et al. |
| 2015/0041347 A1 | 2/2015 | Hodgkinson |
| 2015/0122872 A1* | 5/2015 | Olson et al. ..... A61B 17/07292 227/179.1 |
| 2015/0133995 A1 | 5/2015 | Shelton, IV et al. |
| 2015/0157321 A1 | 6/2015 | Zergiebel et al. |
| 2015/0196296 A1* | 7/2015 | Swayze et al. .. A61B 17/07207 227/176.1 |
| 2015/0209045 A1 | 7/2015 | Hodgkinson et al. |
| 2015/0231409 A1* | 8/2015 | Racenet et al. .. A61B 17/07292 227/175.1 |
| 2015/0297236 A1* | 10/2015 | Harris et al. ........ A61B 17/0684 227/176.1 |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1* | 5/2016 | Baxter, III et al. .. A61B 17/105 227/176.1 |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0278765 A1* | 9/2016 | Shelton, IV et al. ...................... A61B 17/07207 |
| 2016/0278776 A1* | 9/2016 | Shelton, IV et al. . A61B 17/068 |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0055981 A1* | 3/2017 | Vendely et al. .. A61B 17/07292 |
| 2017/0079653 A1* | 3/2017 | Kostrzewski .... A61B 17/07292 |
| 2017/0119390 A1* | 5/2017 | Schellin et al. .. A61B 17/07207 |
| 2017/0150967 A1 | 6/2017 | Hodgkinson et al. |
| 2017/0172575 A1* | 6/2017 | Hodgkinson ......... A61B 17/1155 |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1* | 12/2017 | Casasanta, Jr. et al. ...................... A61B 17/068 |
| 2018/0125491 A1* | 5/2018 | Aranyi ............ A61B 17/07207 |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0235625 A1* | 8/2018 | Shelton, IV et al. ...................... A61B 17/07292 |
| 2018/0250000 A1* | 9/2018 | Hodgkinson et al. A61N 5/1007 |
| 2018/0256164 A1* | 9/2018 | Aranyi ............... A61B 5/6858 |
| 2018/0296214 A1 | 10/2018 | Hodgkinson et al. |
| 2018/0310937 A1 | 11/2018 | (Prommersberger) Stopek |
| 2019/0021734 A1 | 1/2019 | Hodgkinson |
| 2019/0038285 A1* | 2/2019 | Mozdzierz ...... A61B 17/07292 |
| 2019/0059878 A1 | 2/2019 | (Tarinelli) Racenet et al. |
| 2019/0059896 A1* | 2/2019 | Beardsley ....... A61B 17/07292 |
| 2019/0083087 A1 | 3/2019 | Viola et al. |
| 2019/0343521 A1* | 11/2019 | Williams et al. A61B 17/07292 |
| 2020/0246008 A1* | 8/2020 | (Prommersberger) Stopek ......... A61B 17/105 |

(56) References Cited

U.S. PATENT DOCUMENTS

| | | | |
|---|---|---|---|
| 2021/0113206 A1* | 4/2021 | Shelton, IV et al. | ......................... A61B 17/07207 |
| 2021/0290227 A1* | 9/2021 | Mandula et al. | A61B 17/07292 |
| 2021/0290230 A1* | 9/2021 | Fernandes et al. | A61B 17/07207 |
| 2022/0000480 A1* | 1/2022 | Diaz-Chiosa | ......... A61M 5/007 |
| 2022/0117600 A1* | 4/2022 | Abramek et al. | .... A61B 17/072 |
| 2023/0066004 A1* | 3/2023 | Baril et al. | ....... A61B 17/07207 |

FOREIGN PATENT DOCUMENTS

| | | | |
|---|---|---|---|
| DE | 19924311 | A1 | 11/2000 |
| EP | 0327022 | A2 | 8/1989 |
| EP | 0594148 | A1 | 4/1994 |
| EP | 2491867 | A1 | 8/2012 |
| JP | 2000166933 | A | 6/2000 |
| JP | 2002202213 | A | 7/2002 |
| JP | 2007124166 | A | 5/2007 |
| JP | 2010214132 | A | 9/2010 |
| WO | 9005489 | A1 | 5/1990 |
| WO | 95/16221 | A1 | 6/1995 |
| WO | 9838923 | A1 | 9/1998 |
| WO | 9926826 | A2 | 6/1999 |
| WO | 0010456 | A1 | 3/2000 |
| WO | 0016684 | A1 | 3/2000 |
| WO | 2010075298 | A2 | 7/2010 |

OTHER PUBLICATIONS

Australian Examination Report No. 1 corresponding to AU 2012227358 dated May 16, 2016.
Australian Examination Report No. 1 corresponding to AU 2012244169 dated May 10, 2016.
Australian Examination Report No. 1 corresponding to AU 2012244380 dated May 20, 2016.
Australian Examination Report No. 1 corresponding to AU 2012254977 dated May 30, 2016.
Australian Examination Report No. 1 corresponding to AU 2013206777 dated Feb. 1, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2013213767 dated Jun. 29, 2017.
Australian Examination Report No. 1 corresponding to AU 2013234418 dated Jul. 14, 2017.
Australian Examination Report No. 1 corresponding to AU 2013234420 dated Oct. 24, 2017.
Australian Examination Report No. 1 corresponding to AU 2013266989 dated Jul. 10, 2017.
Australian Examination Report No. 1 corresponding to AU 2014200074 dated Jul. 20, 2017.
Australian Examination Report No. 1 corresponding to AU 2014200109 dated Jul. 20, 2017.
Australian Examination Report No. 1 corresponding to AU 2014200584 dated Jun. 15, 2015.
Australian Examination Report No. 1 corresponding to AU 2014200793 dated Sep. 2, 2017.
Australian Examination Report No. 1 corresponding to AU 2014201008 dated May 23, 2017.
Australian Examination Report No. 1 corresponding to AU 2014227480 dated May 21, 2016.
Australian Examination Report No. 1 corresponding to Patent Application AU 2017225037 dated Jan. 23, 2018.
Australian Examination Report No. 2 corresponding to AU 2012261752 dated Jul. 7, 2017.
Australian Patent Examination Report No. 1 corresponding to AU 2012244382 dated Jul. 10, 2016.
Australian Patent Examination Report No. 1 corresponding to AU 2012250278 dated Jul. 10, 2016.
Australian Patent Examination Report No. 1 corresponding to AU 2012261752 dated Sep. 6, 2016.
Australian Patent Examination Report No. 1 corresponding to AU 2012268923 dated Sep. 28, 2016.
Canadian First Office Action corresponding to CA 2,686,105 dated Sep. 17, 2015.
Canadian Office Action corresponding to CA 2,665,206 dated Nov. 19, 2013.
Canadian Office Action corresponding to CA 2,696,419 dated Jan. 14, 2016.
Canadian Office Action corresponding to CA 2,697,819 dated Jan. 6, 2016.
Canadian Office Action corresponding to CA 2,712,617 dated Jun. 30, 2016.
Canadian Office Action corresponding to Patent Application CA 2,790,743 dated May 14, 2018.
Chinese First Office Action corresponding to CN 201210544552 dated Nov. 23, 2015.
Chinese First Office Action corresponding to CN 201210545228 dated Nov. 30, 2015.
Chinese First Office Action corresponding to CN 2013103036903 dated Jun. 30, 2016.
Chinese First Office Action corresponding to CN 201310353628.5 dated Jan. 25, 2016.
Chinese First Office Action corresponding to CN 201310646606.8 dated Dec. 23, 2016.
Chinese First Office Action corresponding to CN 2013107068710 dated Dec. 16, 2016.
Chinese First Office Action corresponding to CN 201410028462.4 dated Mar. 2, 2017.
Chinese First Office Action corresponding to CN 201410084070 dated Mar. 13, 2017.
Chinese First Office Action corresponding to CN 201410449019.4 dated Mar. 30, 2016.
Chinese First Office Action corresponding to CN 201410778512.0 dated May 13, 2016.
Chinese First Office Action corresponding to Patent Application CN 201410588811.8 dated Dec. 5, 2017.
Chinese First Office Action corresponding to Patent Application CN 201610279682.3 dated Jan. 10, 2018.
Chinese Notification of Reexamination corresponding to CN 201010517292.8 dated Jun. 2, 2015.
Chinese Office Action corresponding to CN 201010517292.8 dated Jun. 2, 2015.
Chinese Office Action corresponding to CN 201210129787.2 dated Aug. 24, 2015.
Chinese Office Action corresponding to CN 201210545228 dated Jun. 29, 2016.
Chinese Second Office Action corresponding to CN 2013103036903 dated Feb. 23, 2017.
Chinese Second Office Action corresponding to CN 201310353628.5 dated Sep. 26, 2016.
Chinese Second Office Action corresponding to Patent Application CN 201410588811.8 dated Aug. 27, 2018.
Chinese Second Office Action corresponding to Patent Application CN 201610279682.3 dated Aug. 8, 2018.
Copy of European Search Report corresponding to EP 05 80 4382.9, completed Oct. 5, 2010 and mailed Oct. 12, 2010; (3 pp).
Copy of European Search Report corresponding to EP 06 00 4598, completed Jun. 22, 2006; (2 pp).
Copy of European Search Report corresponding to EP 06 01 6962.0, completed Jan. 3, 2007 and mailed Jan. 11, 2007; (10 pp).
Copy of European Search Report corresponding to EP 08 25 1779, completed Jul. 14, 2008 and mailed Jul. 23, 2008; (5 pp).
Copy of European Search Report corresponding to EP 08 25 1989.3, completed Mar. 11, 2010 and mailed Mar. 24, 2010; (6 pp).
Copy of European Search Report corresponding to EP 09 25 2897.5, completed Feb. 7, 2011 and mailed Feb. 15, 2011; (3 pp).
Copy of European Search Report corresponding to EP 10 25 0639.1, completed Jun. 17, 2010 and mailed Jun. 28, 2010; (7 pp).
Copy of European Search Report corresponding to EP 10 25 0642.5, completed Mar. 25, 2011 and mailed Apr. 4, 2011; (4 pp).

(56) References Cited

OTHER PUBLICATIONS

Copy of European Search Report corresponding to EP 10 25 0715.9, completed Jun. 30, 2010 and mailed Jul. 20, 2010; (3 pp).
Copy of European Search Report corresponding to EP 12 15 0511.9, completed Apr. 16, 2012 and mailed Apr. 24, 2012; (7 pp).
Copy of European Search Report corresponding to EP 12 15 2229.6, completed Feb. 23, 2012 and mailed Mar. 1, 2012; (4 pp).
Copy of European Search Report corresponding to EP 12 15 2541.4, completed Apr. 23, 2012 and mailed May 3, 2012; (10 pp).
Copy of European Search Report corresponding to EP 12 15 8861.0, completed Jul. 17, 2012 and mailed Jul. 24, 2012; (9 pp).
Copy of European Search Report corresponding to EP 12 16 5609.4, completed Jul. 5, 2012 and mailed Jul. 13, 2012; (8 pp).
Copy of European Search Report corresponding to EP 12 16 5878.5, completed Jul. 24, 2012 and mailed Aug. 6, 2012; (8 pp).
Copy of Extended European Search Report corresponding to EP 07 00 5842.5, completed May 13, 2013 and mailed May 29, 2013; (7 pp).
Copy of Extended European Search Report corresponding to EP 12 18 6175.1, completed Jan. 15, 2013 and mailed Jan. 23, 2013; (7 pp).
Copy of Extended European Search Report corresponding to EP 12 19 1035.0, completed Jan. 11, 2013 and mailed Jan. 18, 2013; (7 pp).
Copy of Extended European Search Report corresponding to EP 12 19 1114.3, completed Jan. 23, 2013 and mailed Jan. 31, 2013; (10 pp).
Copy of Extended European Search Report corresponding to EP 12 19 2224.9, completed Mar. 14, 2013 and mailed Mar. 26, 2013; (8 pp).
Copy of Extended European Search Report corresponding to EP 12 19 6904.2, completed Mar. 28, 2013 and mailed Jul. 26, 2013; (8 pp).
Copy of Extended European Search Report corresponding to EP 12 19 6911.7, completed Apr. 18, 2013 and mailed Apr. 24, 2013; (8 pp).
Copy of Extended European Search Report corresponding to EP 12 19 8749.9, completed May 21, 2013 and mailed May 31, 2013; (8 pp).
Copy of Extended European Search Report corresponding to EP 12 19 8776.2, completed May 16, 2013 and mailed May 27, 2013; (8 pp).
Copy of Extended European Search Report corresponding to EP 13 15 6297.7, completed Jun. 4, 2013 and mailed Jun. 13, 2013; (7 pp).
Copy of Extended European Search Report corresponding to EP 13 17 3985.6, completed Aug. 19, 2013 and mailed Aug. 28, 2013; (6 pp).
Copy of Extended European Search Report corresponding to EP 13 17 3986.4, completed Aug. 20, 2013 and mailed Aug. 29, 2013; (6 pp).
Copy of International Search Report corresponding to International Application No. PCT/US2005/036740, completed Feb. 20, 2007 and mailed Mar. 23, 2007; (8 pp).
Copy of International Search Report corresponding to International Application No. PCT/US2007/022713, completed Apr. 21, 2008 and mailed May 15, 2008; (1 p).
Copy of International Search Report corresponding to International Application No. PCT/US2008/002981, completed Jun. 9, 2008 and mailed Jun. 26, 2008; (2 pp).
European Communication corresponding to EP 13 17 6895.4 dated Nov. 5, 2015.
European Office Action corresponding to EP 10 25 0715.9 dated May 12, 2016.
European Office Action corresponding to EP 11 18 3256.4 dated Apr. 20, 2016.
European Office Action corresponding to EP 12 15 2541.4 dated Sep. 27, 2016.
European Office Action corresponding to EP 12 16 5609.4 dated Aug. 5, 2016.
European Office Action corresponding to EP 12 186 175.1 dated Jun. 1, 2015.
European Office Action corresponding to EP 12 19 4784.0 dated May 29, 2017.
European Office Action corresponding to EP 12 19 8776.2 dated Jan. 19, 2016.
European Office Action corresponding to EP 12 19 8776.2 dated Sep. 12, 2016.
European Office Action corresponding to EP 12 198 776.2 dated Apr. 7, 2015.
European Office Action corresponding to EP 13 156 297.7 dated Apr. 10, 2015.
European Office Action corresponding to EP 13 17 3986.4 dated Nov. 29, 2017.
European Office Action corresponding to EP 13 180 881.8 dated Jun. 19, 2015.
European Office Action corresponding to EP 13 19 7958.5 dated Dec. 11, 2017.
European Office Action corresponding to EP 14 15 2060.1 dated Aug. 4, 2016.
European Office Action corresponding to EP 14 15 7997.9 dated Jun. 29, 2016.
European Office Action corresponding to EP 14 157 195.0 dated Jul. 2, 2015.
European Office Action corresponding to EP 14 17 2681.0 dated May 13, 2016.
European Office Action corresponding to EP 15 15 2392.5 dated Aug. 8, 2016.
European Office Action corresponding to EP 15 17 4146.9 dated May 15, 2017.
European Office Action corresponding to Patent Application EP 14 15 7195.0 dated Jun. 12, 2018.
European Office Action corresponding to Patent Application EP 16 16 6367.9 dated Dec. 11, 2017.
Extended European Search Report corresponding to EP 07 86 1534.1, completed Sep. 20, 2013 and mailed Sep. 30, 2013; (5 pp).
Extended European Search Report corresponding to EP 08 72 6500.5, completed Feb. 20, 2014 and mailed Mar. 3, 2014; (7 pp).
Extended European Search Report corresponding to EP 10 25 1795.0, completed Dec. 11, 2013 and mailed Dec. 20, 2013; (6 pp).
Extended European Search Report corresponding to EP 12 19 6902.6 dated Aug. 6, 2015.
Extended European Search Report corresponding to EP 12 19 6912.5 dated Feb. 1, 2016.
Extended European Search Report corresponding to EP 12 19 8753.1 dated Feb. 24, 2016.
Extended European Search Report corresponding to EP 13 15 4571 7, completed Oct. 10, 2014 and mailed Oct. 20, 2014; (8 pp).
Extended European Search Report corresponding to EP 13 17 1856.1, completed Oct. 29, 2013 and mailed Nov. 7, 2013; (8 pp).
Extended European Search Report corresponding to EP 13 17 6895.4, completed Nov. 29, 2013 and mailed Dec. 12, 2013; (5 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 18 2911.1, completed Dec. 2, 2013 and mailed Dec. 16, 2013; (8 pp).
Extended European Search Report corresponding to EP 13 18 3876.5, completed Oct. 14, 2013 and mailed Oct. 24, 2013; (5 pp).
Extended European Search Report corresponding to EP 13 18 7911.6, completed Jan. 22, 2014 and mailed Jan. 31, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 4995 0, completed Jun. 5, 2014 and mailed Oct. 13, 2014; (10 pp).

(56) References Cited

OTHER PUBLICATIONS

Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 14 15 2060.1 dated Aug. 14, 2015.
Extended European Search Report corresponding to EP 14 15 3609.4 dated Jul. 14, 2017.
Extended European Search Report corresponding to EP 14 15 3610.2 dated Jul. 17, 2017.
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
Extended European Search Report corresponding to EP 14 15 7997 9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 14 16 9739.1, completed Aug. 19, 2014 and Aug. 29, 2014; (7 pp).
Extended European Search Report corresponding to EP 14 17 4814.5 dated Jun. 9, 2015.
Extended European Search Report corresponding to EP 14 18 1125 7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419 3, completed Mar. 24, 2015 and mailed Mar. 30, 2015; (6 pp).
Extended European Search Report corresponding to EP 15 17 4146.9 dated Jan. 20, 2016.
Extended European Search Report corresponding to EP 15 18 0491.1 dated Dec. 9, 2015.
Extended European Search Report corresponding to EP 15 18 3819.0 dated Dec. 11, 2015.
Extended European Search Report corresponding to EP 16 15 0232.3 dated Apr. 12, 2016.
Extended European Search Report corresponding to EP 16 15 3647.9 dated Jun. 3, 2016.
Extended European Search Report corresponding to EP 16 16 6367.9 dated Jan. 16, 2017.
Extended European Search Report corresponding to EP 16 19 6549.6 dated Mar. 17, 2017.
Extended European Search Report corresponding to EP 17 17 5656.2 dated Nov. 7, 2017.
Extended European Search Report corresponding to EP 17 17 8528.0 dated Oct. 13, 2017.
Extended European Search Report corresponding to Patent Application EP 12196912.5 dated Feb. 1, 2016.
Extended European Search Report corresponding to Patent Application EP 18160809.2 dated Sep. 18, 2018.
Extended European Search Report corresponding to Patent Application EP 18190154.7 dated Feb. 4, 2019.
Extended European Search Report corresponding to Patent Application EP 18192317.8 dated Dec. 20, 2018.
International Search Report and Written Opinion dated Jan. 23, 2023, issued in corresponding international appln. No. PCT/IB2022/057648, 17 pages.
Japanese Office Action corresponding to 2012-255242 mailed Jul. 26, 2016.
Japanese Office Action corresponding to JP 2012-040188 mailed May 17, 2016.
Japanese Office Action corresponding to JP 2012-040188 mailed Oct. 21, 2015.
Japanese Office Action corresponding to JP 2012-098903 mailed Feb. 22, 2016.
Japanese Office Action corresponding to JP 2012-250058 mailed Jun. 29, 2016.
Japanese Office Action corresponding to JP 2012-268668 mailed Jul. 27, 2016.
Japanese Office Action corresponding to JP 2013-000321 dated Jan. 4, 2017.
Japanese Office Action corresponding to JP 2013-000321 mailed Sep. 13, 2016.
Japanese Office Action corresponding to JP 2013-003624 mailed Aug. 25, 2016.
Japanese Office Action corresponding to JP 2013-147701 dated Mar. 21, 2017.
Japanese Office Action corresponding to JP 2013-147701 mailed Oct. 27, 2017.
Japanese Office Action corresponding to JP 2013-154561 mailed May 23, 2017.
Japanese Office Action corresponding to JP 2013-169083 mailed May 31, 2017.
Japanese Office Action corresponding to JP 2013-175379 dated Mar. 1, 2017.
Japanese Office Action corresponding to JP 2013-175379 mailed Oct. 20, 2017.
Japanese Office Action corresponding to JP 2013-229471 mailed Aug. 17, 2017.
Japanese Office Action corresponding to JP 2013-250857 mailed Aug. 17, 2017.
Japanese Office Action corresponding to JP 2014-009738 mailed Nov. 14, 2017.
Japanese Office Action corresponding to JP 2014-216989 mailed Sep. 11, 2015.
Japanese Office Action corresponding to JP 2014-252703 mailed Sep. 26, 2016.
Japanese Office Action corresponding to JP 2017-075975 mailed Dec. 4, 2017.
Japanese Office Action corresponding to Patent Application JP 2013-154561 mailed Jan. 15, 2018.
Japanese Office Action corresponding to Patent Application JP 2013-229471 mailed May 1, 2018.

\* cited by examiner

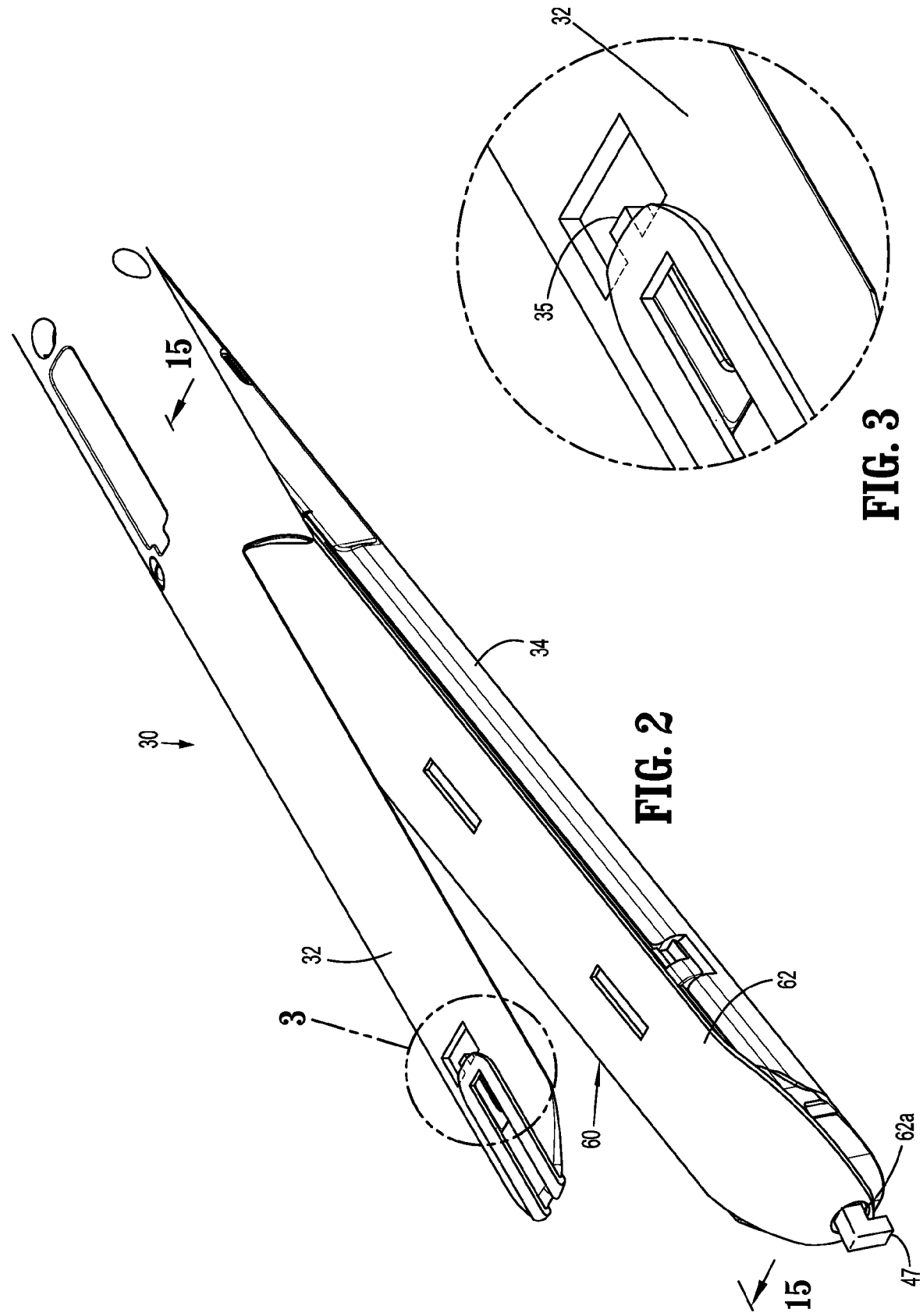

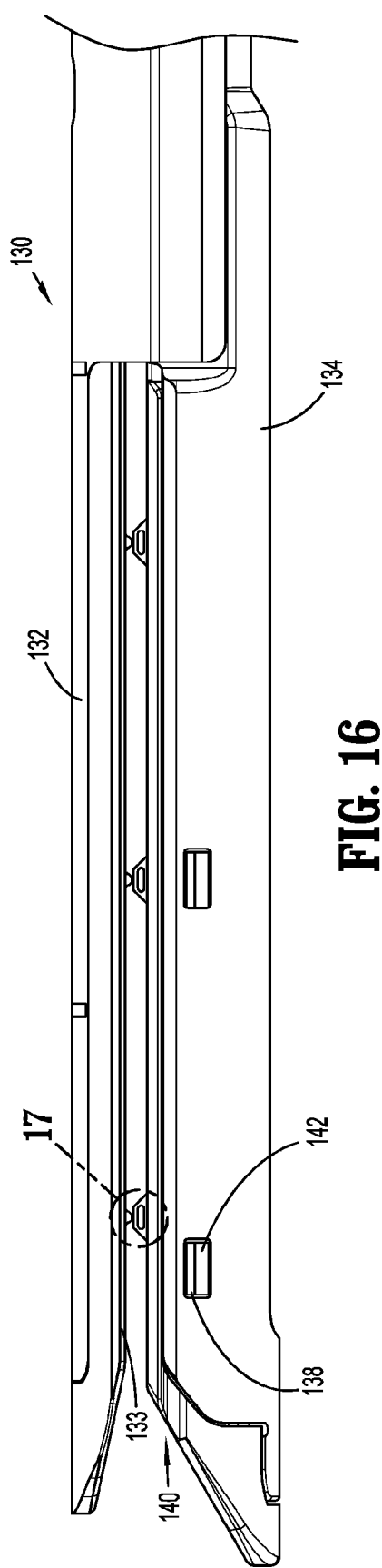
FIG. 16
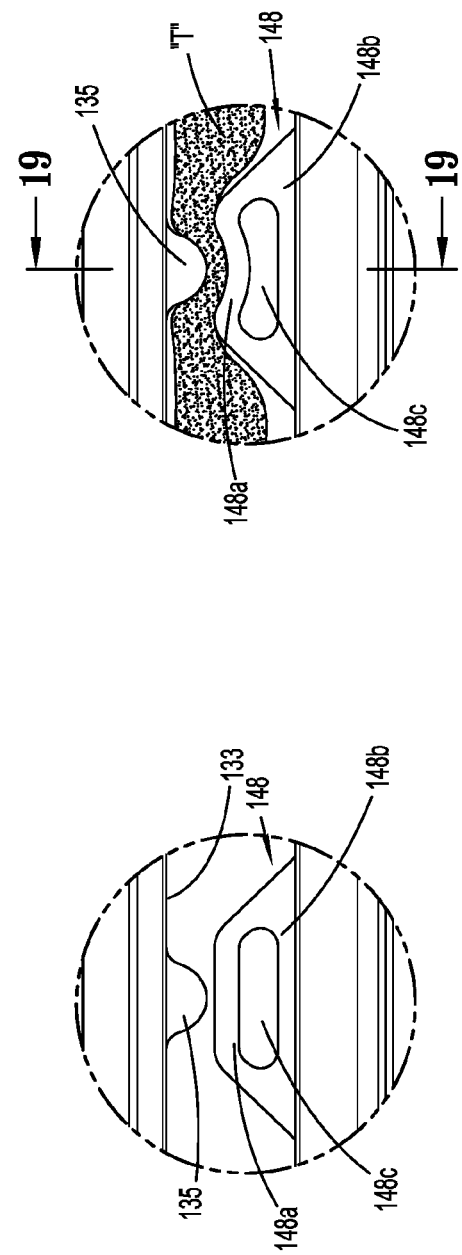
FIG. 18
FIG. 17

ASSEMBLIES FOR SURGICAL STAPLING INSTRUMENTS

FIELD

The present disclosure generally relates to surgical instruments. In particular, the present disclosure relates to assemblies for surgical stapling instruments.

BACKGROUND

Surgical stapling apparatuses are employed by surgeons to sequentially or simultaneously apply one or more rows of fasteners, e.g., staples or two-part fasteners, to body tissue for the purpose of joining segments of body tissue together. Such apparatus generally includes a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure or utilize a surgical stapling apparatus including buttress materials pre-installed thereon, e.g., by an expensive automated attachment process. The buttress material reinforces the staple or suture line as well as covers the juncture of the body tissues to reduce leakage prior to healing.

Typically, buttress solutions may be delivered in several individual steps. One section of the buttress is pre-loaded on a cartridge and a separate section must be applied to an anvil side of the surgical stapler after the cartridge has been loaded.

Surgical stapling devices for performing anastomoses are well known in the art, and typically include an anvil assembly that is movable relative to a cartridge assembly to compress, and subsequently, staple tissue therebetween. The tissue is compressed as the anvil assembly is pivoted relative to the cartridge assembly to create a clamping action. Once a tissue gap, e.g., a distance between the anvil assembly and the cartridge assembly, achieves a predetermined range, the surgical stapling device may be fired.

Fixation and secure placement of tissue are important when firing staple lines to minimize tissue migration and facilitate placement of the staple line and tissue resection. Nonvariable tissue compression may lead to tissue trauma while a desired compression force regardless of tissue thickness provides benefits.

Thus, a loading assembly that integrates a single piece buttress with the cartridge to streamline the loading process and a tool assembly that provides a desired compression force irrespective of tissue thickness are desirable.

SUMMARY

In accordance with an aspect of the present disclosure, a loading assembly for use with a surgical stapling instrument includes a cartridge having a cartridge body with rows of staple pockets that are configured to retain staples therein. The loading assembly also includes a carrier with a platform adapted to releasably retain the cartridge. The platform includes an arm. The carrier also includes a shell that is laterally spaced from the platform and flexibly coupled thereto. The arm extends through the shell at an acute angle while the shell has a passage that is configured to receive a jaw member of the surgical stapling instrument therethrough. The loading assembly also includes a surgical buttress having distal and proximal regions. The distal region includes a first orifice and a cutout, and the proximal region includes a second orifice. The first orifice is attachable to a peg located in a distal region of the shell and the second orifice is attachable to a post located in a distal region of the cartridge such that a portion of the surgical buttress extends through the passage of the shell. The cutout is configured to receive the arm therethrough.

In an aspect of the present disclosure, the loading assembly may further include a hinge that flexibly couples the shell to the platform.

In one aspect of the present disclosure, the cartridge body may include projections extending laterally therefrom. The projections may be configured to releasably engage studs extending from the platform.

In aspects of the present disclosure, the arm may extend through the cutout.

In another aspect of the present disclosure, the cartridge may be insertable into a channel of the surgical stapling instrument.

In a further aspect of the present disclosure, the cartridge may be partially disposed in the channel of the surgical stapling instrument and the jaw member of the surgical stapling instrument may be disposed in the passage of the shell such that a distal portion of the jaw member may contact the arm.

In an aspect of the present disclosure, proximal movement of the carrier relative to the jaw member may seat the cartridge in the channel.

In yet another aspect of the present disclosure, the shell and platform may be parallel to one another and proximal movement of the carrier relative to the jaw member may space the platform away from the shell defining an acute angle therebetween.

In aspects of the present disclosure, the first orifice may be separated from the peg of the shell and attached to a hook on the jaw member.

In accordance with another aspect of the present disclosure, a loading assembly usable with a surgical instrument includes a cartridge having a cartridge body with rows of staple pockets that are configured to retain staples therein and a carrier. The carrier includes a platform configured to releasably retain the cartridge and a shell laterally spaced from the platform and parallel therewith. The shell includes a passage that is configured to receive a jaw member of the surgical instrument therethrough. An arcuate hinge flexibly connects the platform and the shell. A surgical buttress has a first orifice in a distal region thereof and a second orifice in a proximal region thereof. The first orifice is attachable to a peg located in a distal region of the shell and the second orifice is attachable to a post located in a distal region of the cartridge such that a portion of the surgical buttress extends through the passage of the shell.

In aspects of the present disclosure, the loading assembly may also include an arm extending from the platform at an acute angle thereto and the arm may extend through a cutout of the surgical buttress.

In an aspect of the present disclosure, the cartridge may be partially disposed in a channel of the surgical instrument and the jaw member of the surgical instrument may be disposed in the passage of the shell such that a distal portion of the jaw member contacts the arm.

In another aspect of the present disclosure, proximal movement of the carrier relative to the jaw member may seat the cartridge in the channel.

In a further aspect of the present disclosure, proximal movement of the carrier relative to the jaw member may space the platform away from the shell defining an acute angle therebetween.

In yet an aspect of the present disclosure, the first orifice may be separated from the peg of the shell and attached to a hook on the jaw member.

In an aspect of the present disclosure, the platform may include a keel configured to engage a slot of the cartridge and opposed shoulders may be configured to engage opposed sidewalls of the cartridge thereby aligning the cartridge and the carrier.

According to an aspect of the present disclosure, a tool assembly usable with a surgical stapling instrument includes a first jaw defining a U-shaped channel and a second jaw pivotable relative to the first jaw between an approximated position and a spaced apart position. The tool assembly also includes a cartridge disposed in the U-shaped channel and the cartridge includes protrusions extending from a surface of the cartridge towards the second jaw. An anvil is coupled to the second jaw and includes knobs extending from a surface of the anvil towards the protrusions. The knobs and the protrusions are configured to capture tissue therebetween, wherein the protrusions are partially deformable by the knobs with the second jaw in an approximated position.

In an aspect of the present disclosure, the protrusions and the knobs may be arranged in spaced apart rows extending along a length of the tool assembly.

In another aspect of the present disclosure, the protrusions and knobs may be configured to apply a variable amount of compression to tissue disposed therebetween.

In a further aspect of the present disclosure, each protrusion may have a corresponding knob, the protrusions may be laterally aligned, and the knobs may be laterally aligned.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 2 is an enlarged view of the indicated area of detail shown in FIG. 1;

FIG. 3 is an enlarged view of the indicated area of detail shown in FIG. 2;

FIG. 16 is side view of another tool assembly according to the present disclosure;

FIG. 17 is an enlarged view of the indicated area of detail shown in FIG. 16;

FIG. 18 is an enlarged view of the indicated area of detail shown in FIG. 16 with tissue positioned between an anvil and a cartridge of the tool assembly.

DETAILED DESCRIPTION

Figure 1:
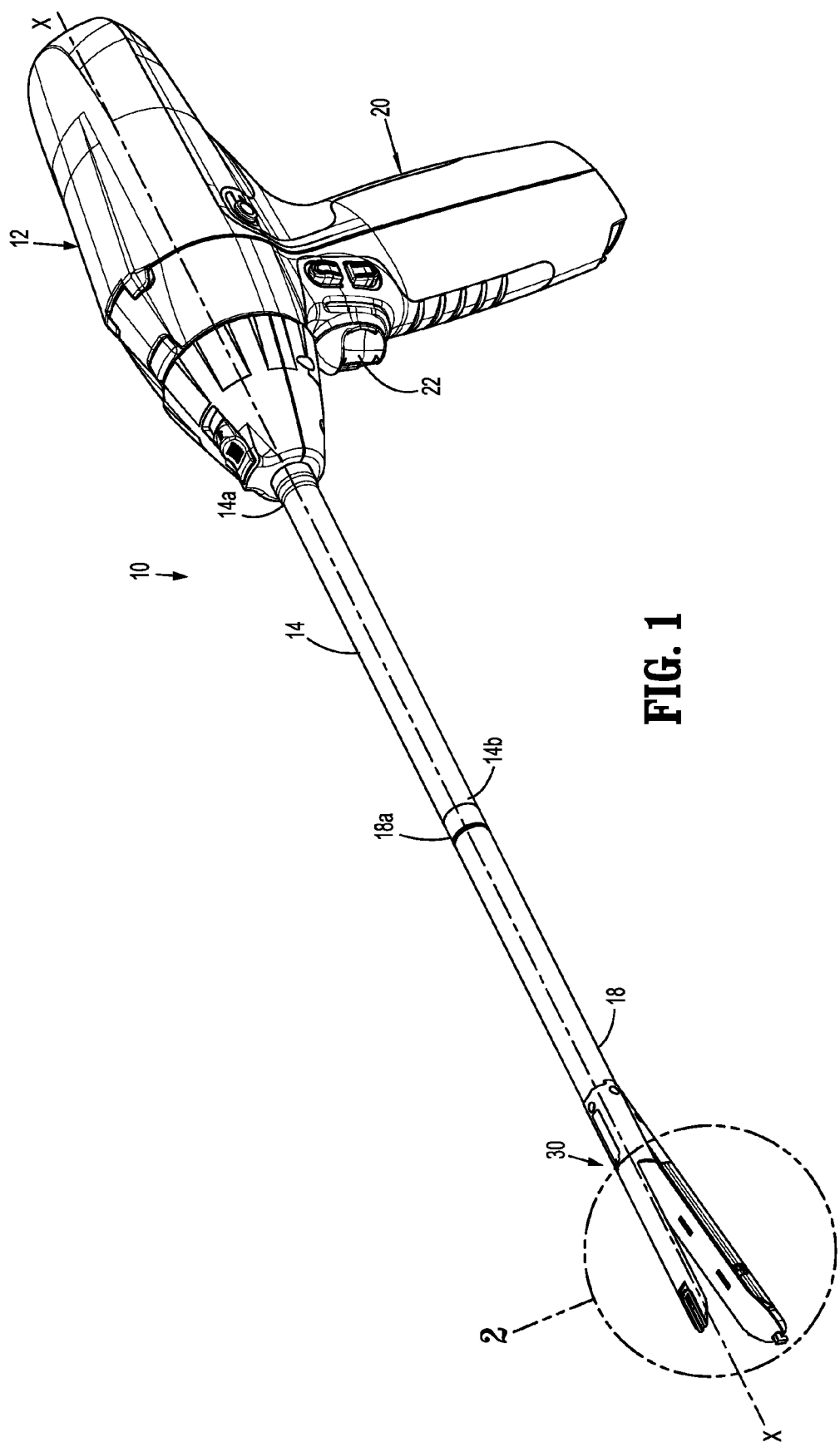
FIG. 1 is a side perspective view of the disclosed stapling device including a tool assembly in an open position.

The disclosed surgical stapling device will now be described in more detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as horizontal, vertical, distal, proximal, and similar terms are used to assist in understanding the description and are not intended to limit the disclosure.

As used herein, the term "distal" refers to the portion of the stapling device that is being described which is further from a user, while the term "proximal" refers to the portion of the stapling device that is being described which is closer to a user. Further, to the extent consistent, any of the aspects and features detailed herein may be used in conjunction with any or all the other aspects and features detailed herein.

As used herein, the terms parallel and perpendicular are understood to include relative configurations that are substantially parallel and substantially perpendicular up to about + or − 10 degrees from true parallel and true perpendicular.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system).

Descriptions of technical features or aspects of the disclosure should typically be considered as available and applicable to other similar features or aspects of the disclosure. Accordingly, technical features described herein according to one exemplary aspect of the disclosure may be applicable to other exemplary aspects of the disclosure, and thus duplicative descriptions may be omitted herein.

FIG. 1 illustrates exemplary aspects of the disclosed surgical stapling instrument shown generally as stapling instrument 10. Stapling instrument 10 includes a powered handle assembly 12, an elongate body 14, and a tool assembly 30. The elongate body 14 defines a longitudinal axis "X-X" and includes a proximal portion 14a supported on the handle assembly 12 and a distal portion 14b that supports the tool assembly 30. In some aspects of the disclosure, the tool assembly 30 forms part of a reload assembly 18 that includes a proximal body portion 18a that is adapted to be releasably coupled to the distal portion 14b of the elongate body 14 of the stapling instrument 10. In other aspects of the disclosure, the proximal body portion 18a includes a distal portion that supports the tool assembly 30 for articulation about an axis transverse to the longitudinal axis "X-X" of the elongate body 14. In alternate aspects of the disclosure, the tool assembly 30 is fixedly secured to the distal portion 14b of the elongate body 14. For a description of exemplary aspects of the tool assembly, see, e.g., U.S. Pat No. 6,241,139 ("the '139 patent").

The handle assembly 12 of the stapling instrument 10 includes a stationary handle 20 and actuation buttons 22 that can be depressed to actuate the tool assembly 30, e.g., approximate the tool assembly 30, articulate the tool assembly 30, fire staples, etc. In aspects of the disclosure, batteries (not shown) are supported in the stationary handle 20 to power the handle assembly 12. It is envisioned that the stapling instrument 10 need not be powered but can also include a manually powered handle assembly such as described in the '139 patent.

Referring now to FIGS. 2 and 3, the tool assembly 30 includes a first jaw member 32 pivotably coupled to a second jaw member 34. The first and second jaw members 32, 34 extend along the longitudinal axis "X-X" of the elongate body 14 and are pivotably coupled in proximal portions thereof. The first jaw member 32 includes an anvil 33 (FIG. 12) with staple deforming concavities (not shown) such as described in the '139 patent. The second jaw member 34 includes a generally U-shaped channel 36 (FIG. 4) that is configured to receive a cartridge 40. The cartridge 40 is releasably retained in the channel 36 due to the interaction between tabs 41 formed along the cartridge 40 and slots 37 formed in the channel 36. Support struts 42 are formed on the cartridge 40 and are positioned to rest on sidewalls 39 of the channel 36 to further stabilize the cartridge 40 within the channel 36. A buttress 60 is coupled to the tool assembly 30 and will be described in further detail hereinafter. One end of the buttress 60 is attached to the first jaw member 32 (FIG. 3) and another end of the buttress 60 is attached to the cartridge 40 disposed in the channel 36 of the second jaw member 34 (FIG. 2).

Figure 4:
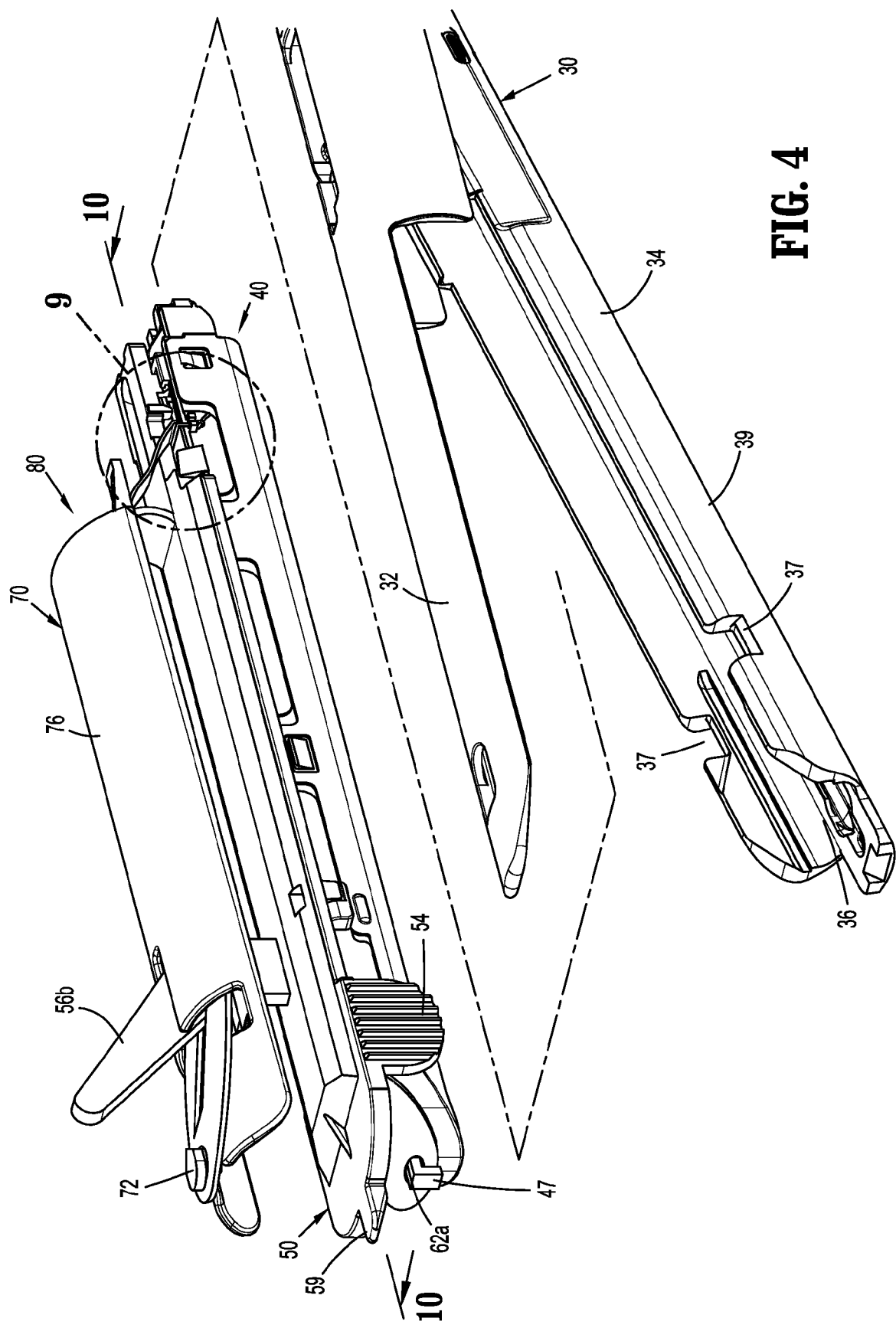
FIG. 4 is an exploded side perspective view of the tool assembly and a loading tool supporting a buttress and a cartridge.
Figure 5:
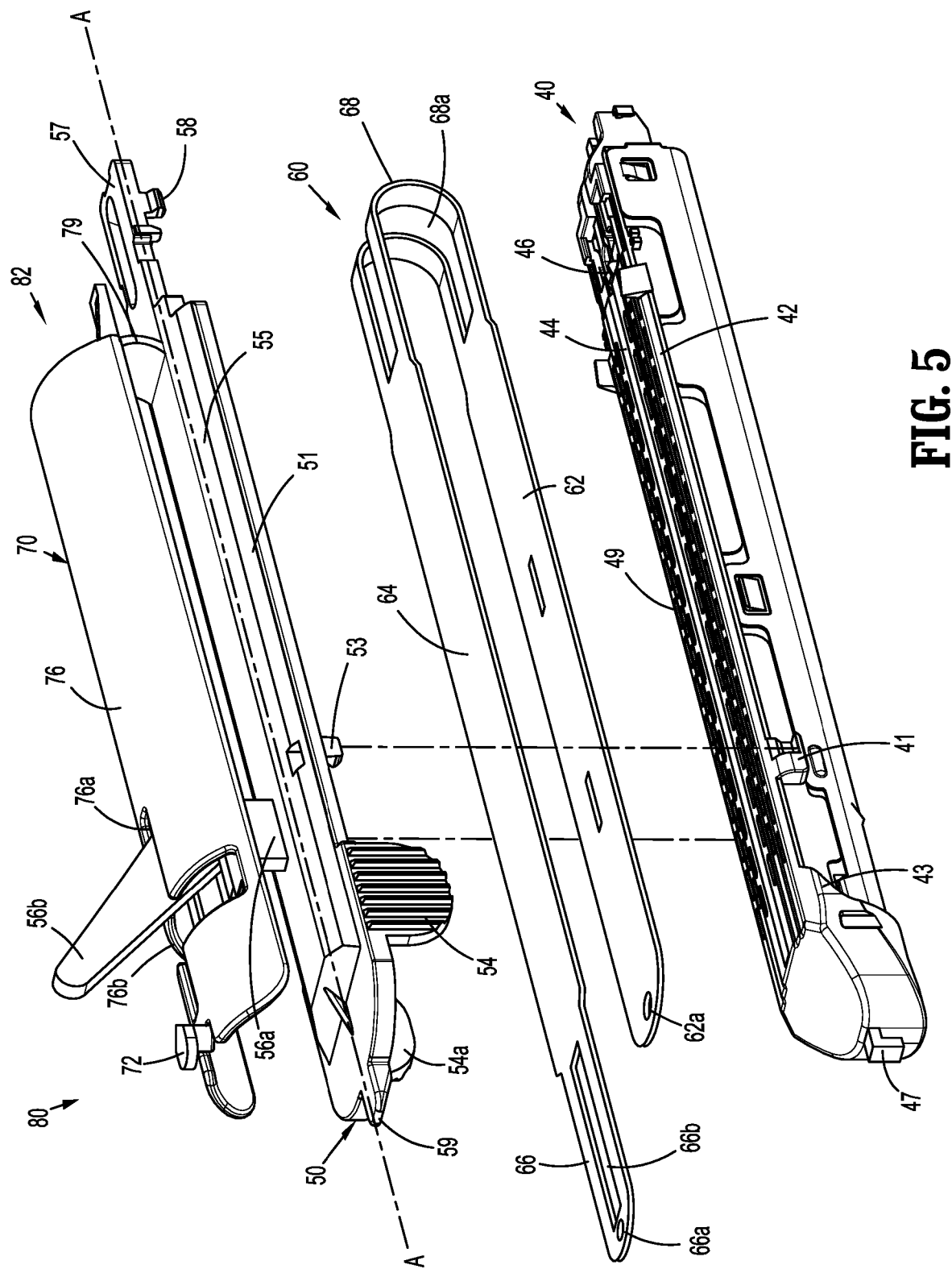
FIG. 5 is an exploded side perspective view of the tool assembly and loading tool of FIG. 4 showing the cartridge disposed in a channel of a first jaw.
Figure 6:
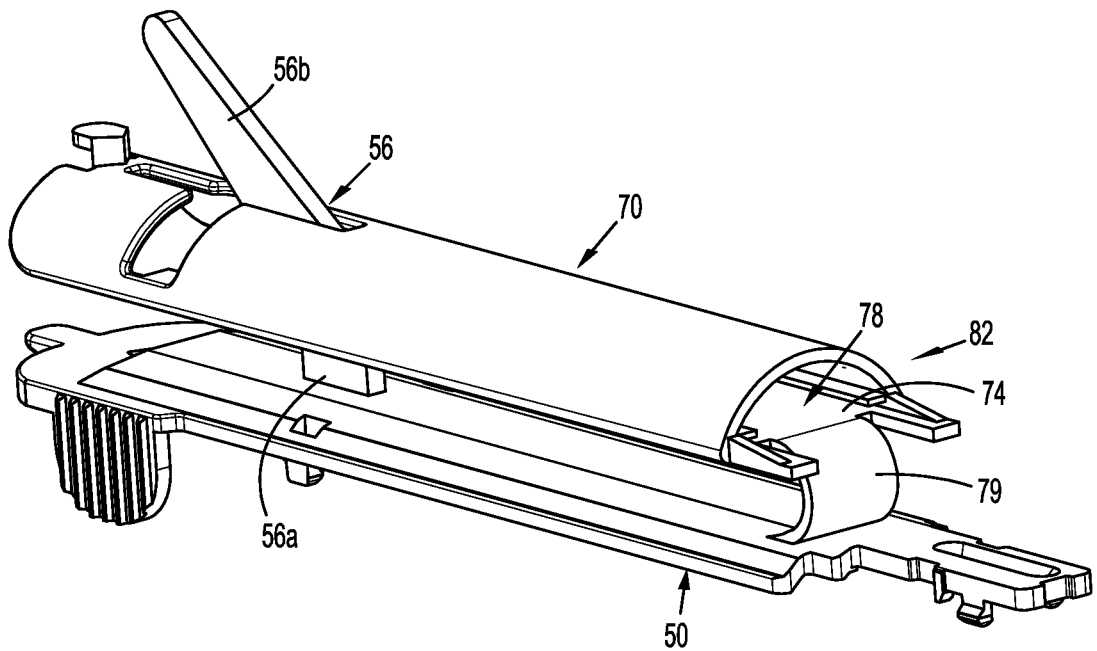
FIG. 6 is side perspective view of the loading tool of FIG. 4 without the buttress and cartridge.
Figure 7:
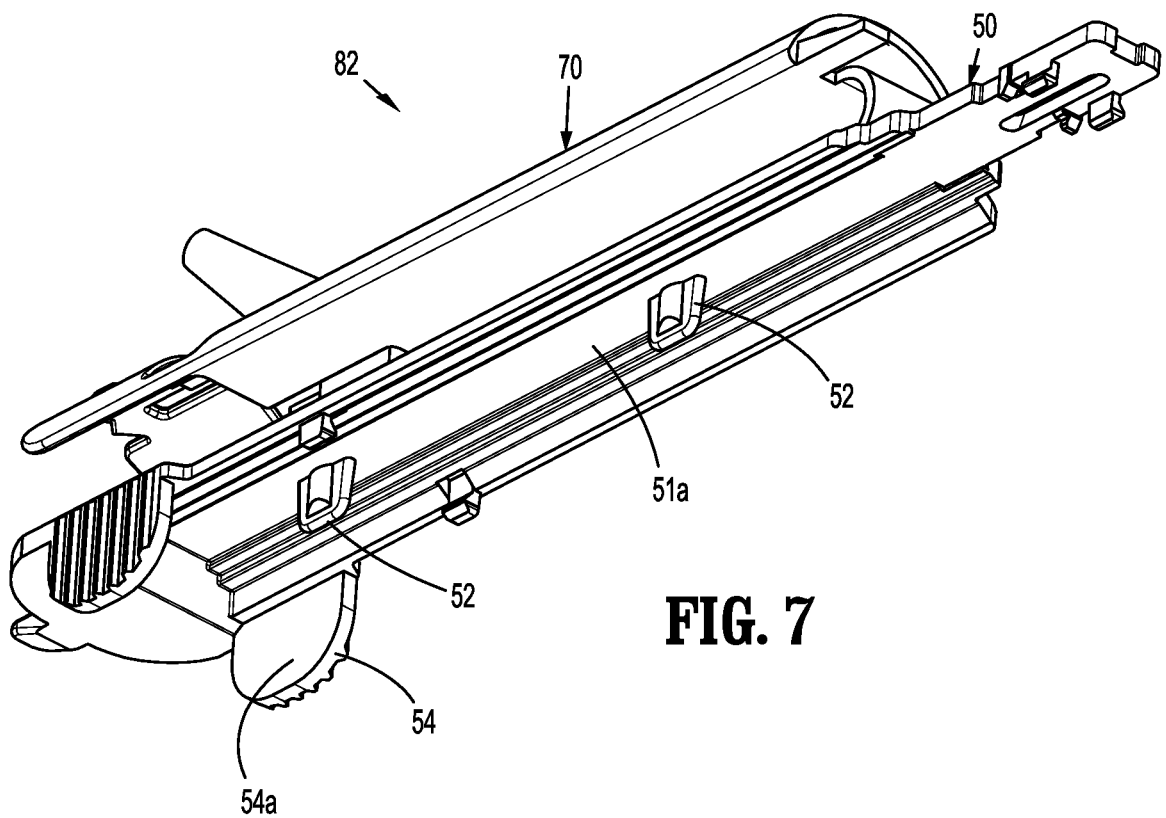
FIG. 7 is a bottom perspective view of the loading tool of FIG. 6.

As seen in FIGS. 4 and 5, the tool assembly 30 is illustrated with the first jaw member 32 spaced apart from the second jaw member 34 and the channel 36 of the second jaw member 34 is shown ready to receive the cartridge 40 therein. A loading assembly 80 includes a carrier 82 usable with the tool assembly 30, the buttress 60, and the cartridge 40. The carrier 82 facilitates coupling the cartridge 40 and the buttress 60 with the tool assembly 30. The carrier 82 has a platform 50 and a shell 70 that extend along a longitudinal axis "A-A". Briefly, a first end of the buttress 60 is attached to a peg 72 located in a distal region of the shell 70 and a second, and opposite end, of the buttress 60 is attached to a post 47 located in a distal region of the cartridge 40. The longitudinal axis "A-A" is parallel with the longitudinal axis "X-X". In an initial or first configuration of the carrier 82, the shell 70 is parallel with the platform 50 and laterally spaced therefrom defining a gap therebetween. The platform 50 of the carrier 82 includes a longitudinally extending deck 51 with shoulders 54 extending from opposed sides of the deck 51, a raised ridge 55 situated atop the deck 51, and a neck 57 extending proximally from the ridge 55. The shoulders 54 are configured to maintain an aligned orientation between the carrier 82 and the cartridge 40. Specifically, outer walls 43 of the cartridge 40 abut inner surfaces 54a of the shoulders 54 of the deck 51 thereby positioning the cartridge 40 relative to the platform 50. With additional reference to FIGS. 6 and 7, a bottom surface 51a of the deck 51 includes keels 52 extending therefrom. The keels 52 are slidably received in a knife channel or knife slot 44 of the cartridge 40. Although shown with two keels 52, it is contemplated that a single keel 52 may be used or more than two keels 52 may be used. Thus, the interaction between the keels 52 and the knife slot 44 of the cartridge 40 in combination with the engagement between the inner surfaces 54a of the shoulders 54 and the outer walls 43 of the cartridge 40 maintain alignment of the cartridge 40 and the platform 50 such that the cartridge 40 lies along the longitudinal axis "A-A". The cartridge 40 is releasably coupled to the deck 51 using the tabs 41 extending laterally from the cartridge 40 that engage studs 53 extending from the deck 51 plus studs 58 that extend from the neck 57 of the platform 50 that engage recesses 46 in a proximal region of the cartridge 40. More particularly, the deck 51 includes studs 53 that extend from the deck 51 away from the shell 70 and towards the cartridge 40. The studs 53 are configured to engage the tabs 41 of the cartridge 40. Two of the studs 53 extend from opposed sides of the deck 51 of the platform 50 in the distal region of the platform 50 and are longitudinally spaced from the shoulders 54 of the deck 51. Additionally, the neck 57 of the platform 50 has a narrower width than the ridge 55 and includes two studs 58 that extend towards the cartridge 40 and are receivable in the recesses 46 of the cartridge 40. Although shown as being longitudinally aligned, it is contemplated that the shoulders 54 and the studs 53 may be longitudinally staggered. Further, the bottom surface 51a of the deck 51 has a stepped configuration that complements a stepped configuration of the cartridge 40. A tab 59 extends from a distal end of the platform 50 and is configured to allow a clinician to separate the carrier 82 from the cartridge 40 by applying a force in a direction away from the cartridge 40 once the cartridge 40 is positioned in the channel 36 of the second jaw member 34.

Figure 13:
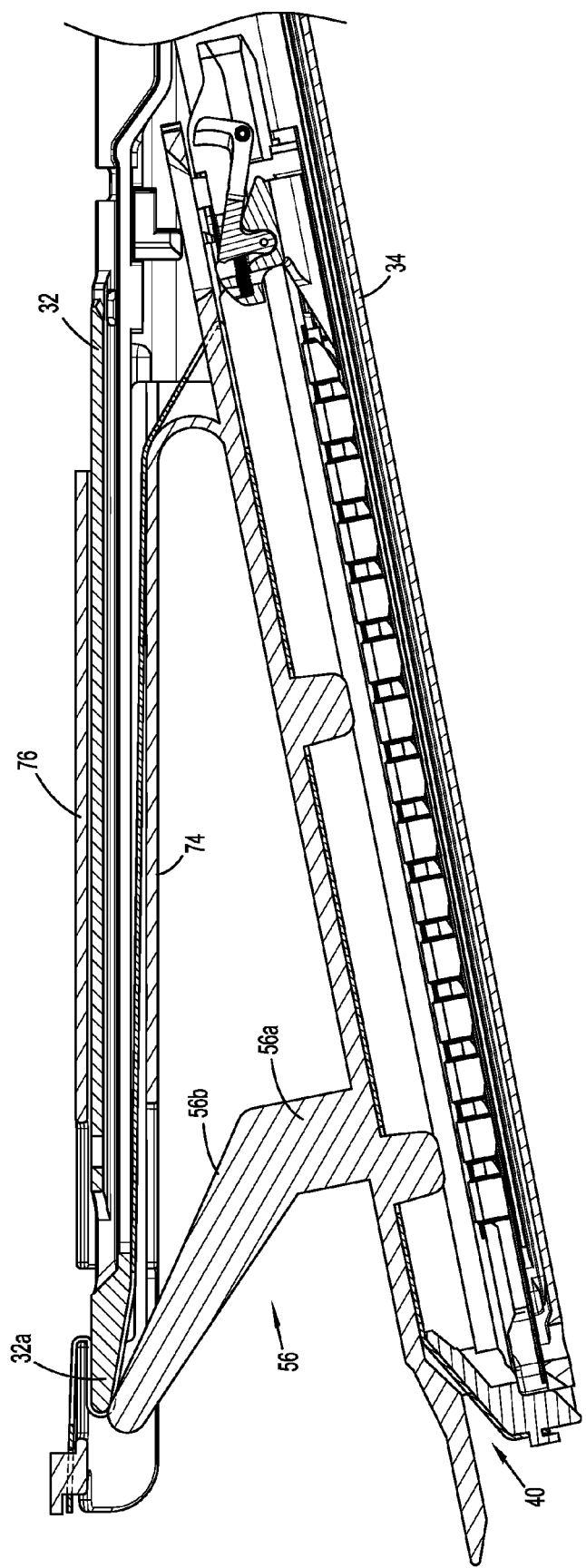
FIG. 13 is the side cross-sectional view of FIG. 12 showing the cartridge loaded in the channel of the first jaw.

The shell 70 of the carrier 82 is flexibly coupled to the platform 50 via a hinge 79. Specifically, one end of the hinge 79 is attached to a proximal region of the raised ridge 55 and another end of the hinge 79 is attached to a proximal end of a shelf 74 of the shell 70. The shelf 74 extends along a length of the shell 70 and is parallel to the platform 50 in the initial configuration of the carrier 82. As the hinge 79 flexibly joins the shelf 74 with the raised ridge 55 of the platform 50, the shelf 74 is transitionable between the initial configuration (FIG. 10) and a deployed or second configuration (FIG. 13) where the shelf 74 is transitioned such that an acute angle is defined between the shelf 74 and the raised ridge 55. An arcuate cover 76 is attached to the shelf 74 and defines a passage 78 between an inside of the arcuate cover 76 and the shelf 74. The passage 78 is configured to receive the first jaw member 32 therein. A distal region of the arcuate cover 76 has a longitudinally extending slot 76a and a laterally extending opening 76b that intersects the slot 76a forming a generally T-shaped aperture through the arcuate cover 76. Additionally, the peg 72 is located at a distal end of the arcuate cover 76 and is configured to couple with a distal orifice 66a of the buttress 60 as will be discussed in detail hereinafter. The raised ridge 55 of the platform 50 has an arm 56 extending therefrom. The arm 56 includes a vertical riser 56a attached to the raised ridge 55 and a finger 56b extending from the riser 56a at an acute angle thereto. The finger extends 56b through the slot 76a in the arcuate cover 76.

Figure 8:
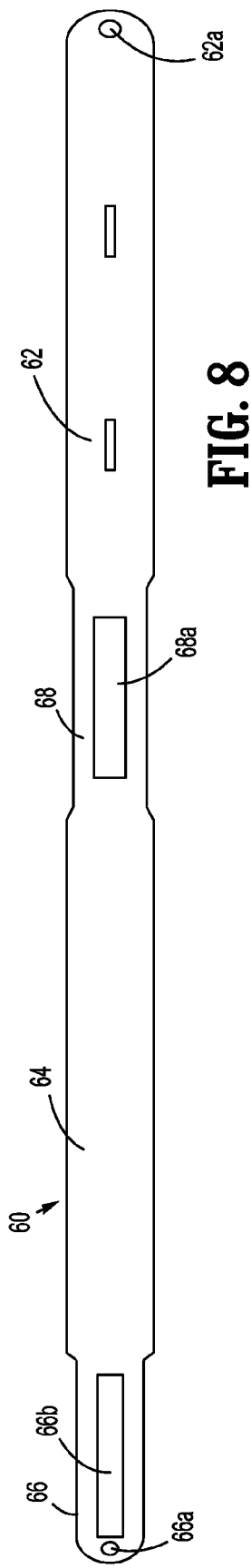
FIG. 8 is a plan view of the buttress of FIG. 5.
Figure 9:
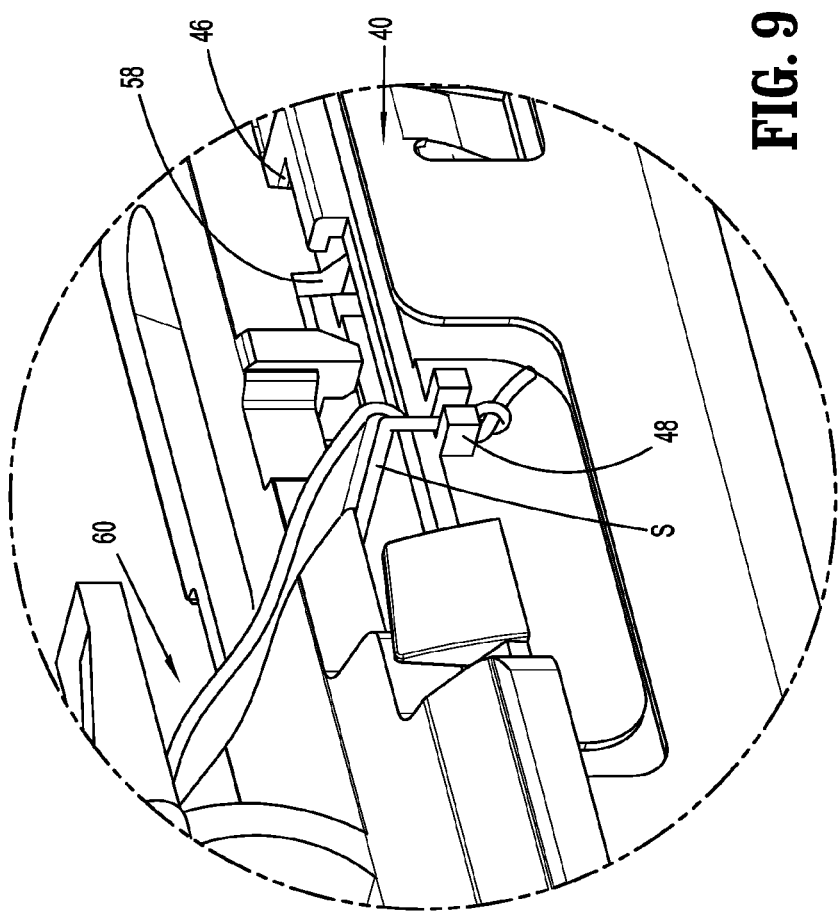
FIG. 9 is an enlarged view of the indicated area of detail shown in FIG. 4.
Figure 10:
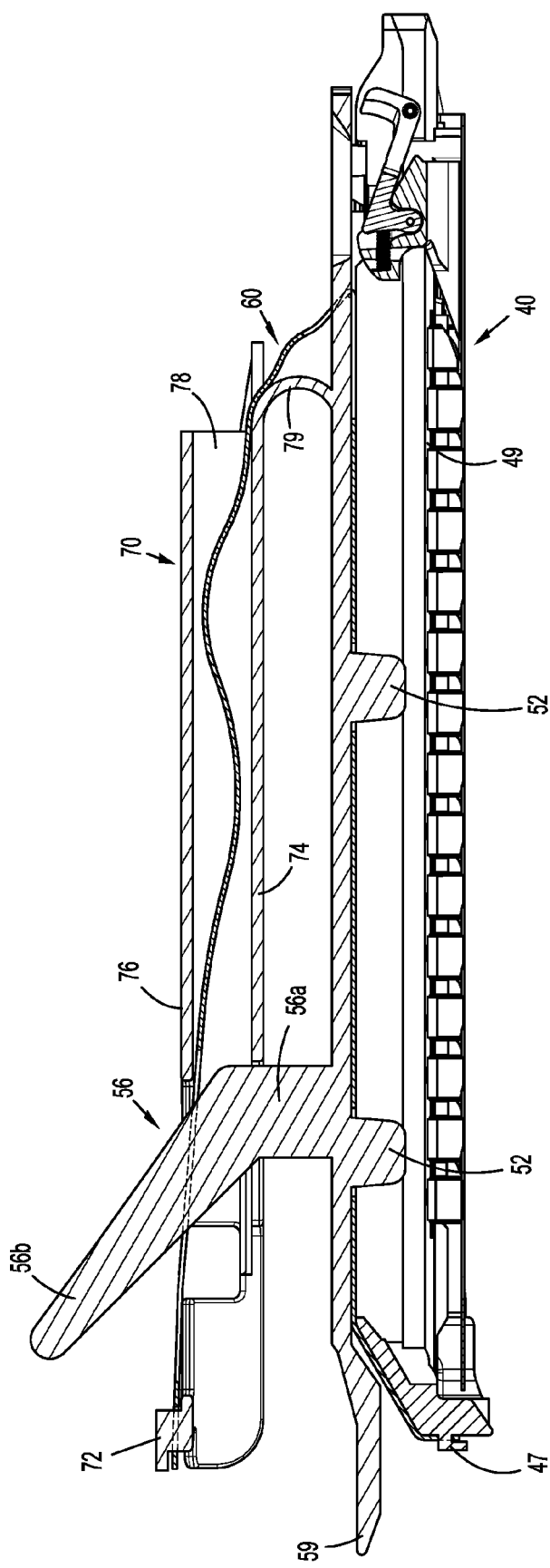
FIG. 10 is a side cross-sectional view of the loading tool and buttress taken along section line 10-10 of FIG. 4.
Figure 11:
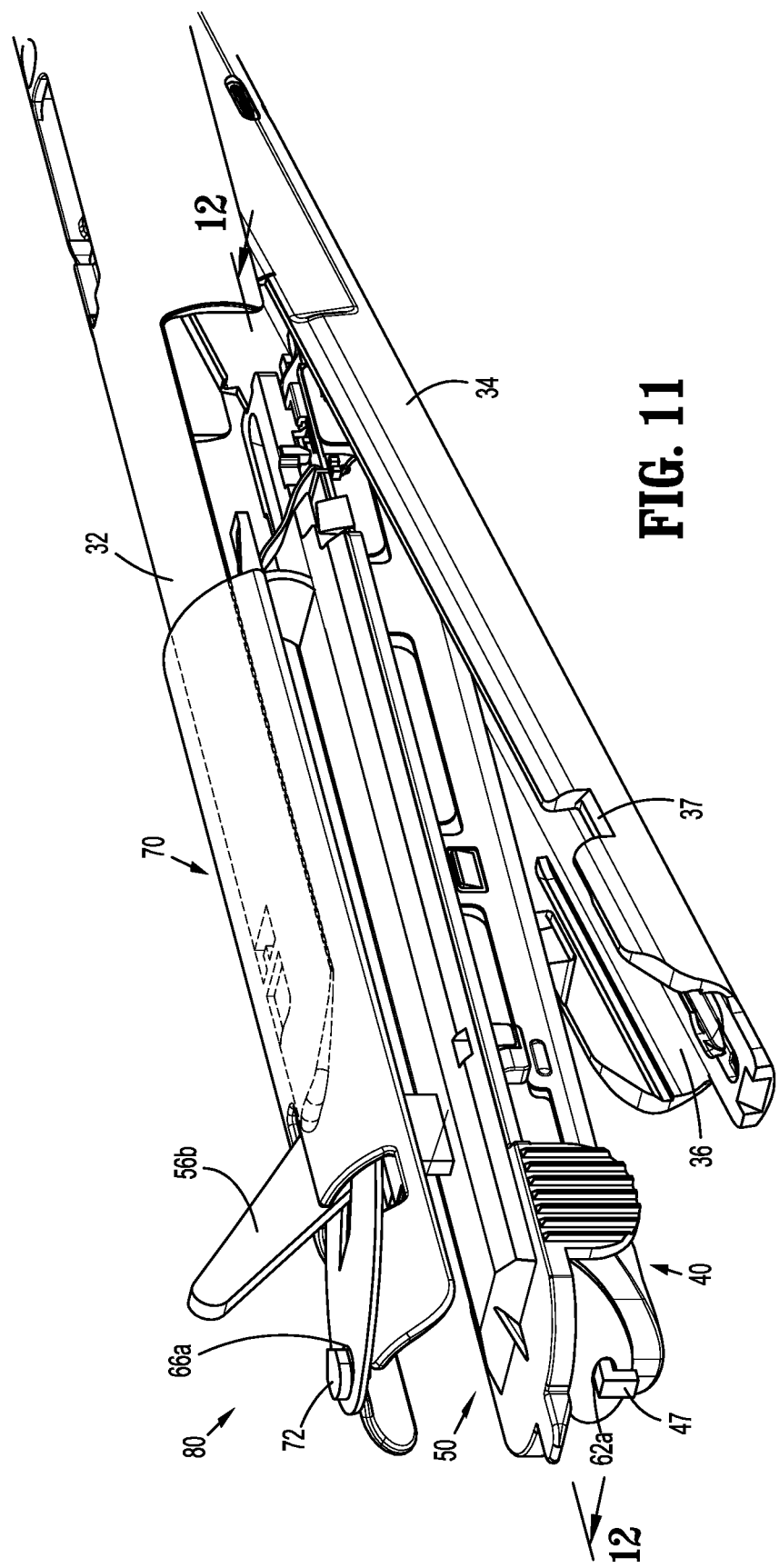
FIG. 11 is a side perspective view of the tool assembly and loading tool of FIG. 4 showing loading the buttress and cartridge onto the tool assembly.

As best shown in FIG. 8, the buttress 60 has an elongated, planar body with a proximal region 62, a distal region 64, and an intermediate region 68 disposed between the proximal and distal regions 62, 64. An extension 66 is attached to the distal region 64 and includes the distal or first orifice 66a and a distal or first cutout 66b. The first orifice 66a is configured to releasably connect to the peg 72 on the arcuate cover 76 of the shell 70 as seen in FIGS. 10 and 11. The first cutout 66b is an elongate opening and is configured to receive the finger 56b of the arm 56 therethrough. The distal region 64 is generally rectangular and configured to abut the anvil 33 of the first jaw member 32. Adjacent to the distal region 64 is the intermediate region 68 with an aperture 68a configured to receive the neck 57 and the hinge 79 therethrough such that the intermediate region 68 wraps around the hinge 79. The proximal region 62 of the buttress 60 includes openings and is configured to abut a tissue contacting surface of the cartridge 40 and cover openings of staple pockets 49 (FIG. 5). Additionally, the proximal region 62 includes a proximal or second orifice 62a that is configured to be attached to the post 47 extending from a distal end of the cartridge 40. As shown in FIGS. 4 and 10, the buttress 60 is attached to the carrier 82 and the cartridge 40 with the first orifice 66a attached to the peg 72 of the arcuate cover 76 and the second orifice 62a attached to the post 47 of the cartridge 40. The buttress 60 is positioned such that the proximal region 62 abuts the tissue contacting surface of the cartridge 40, the intermediate region 68 wraps around the hinge 79, and the distal region 64 extends through the passage 78 of the shell 70. In the absence of the first jaw member 32 being positioned in the passage 78 of the shell 70, the proximal region 62 of the buttress 60 is flush and taut against the tissue contacting surface of the cartridge 40 as it is sandwiched between the tissue contacting surface of the cartridge 40 and the bottom surface 51a of the deck 51 (FIG. 10). The intermediate region 68 and the distal region 64 are slack. As seen in FIGS. 9 and 10, a suture "S" is attached to notches 48 in the cartridge 40 (only one is shown) to secure the buttress 60 to the cartridge 40.

As used herein, "buttress" includes a pledget, gasket, buttress, or staple line reinforcement structure. The buttress 60 can be formed from a thin sheet of plastic or polymeric material. The buttress 60 can be molded, cut, extruded, or otherwise formed from the plastic/polymeric material. The material for the buttress 60 may also be a thin sheet metal or foil. At least a portion of the buttress 60 may be made from a biodegradable material (e.g., natural collagenous materials or synthetic resins) or from a non-biodegradable material (e.g., polyolefins, polyethylene, etc.). The material may be a non-woven material formed by melt-blown or melt-spun methods, a mesh material, a braid material, and/or a molded or extruded sheet.

Figure 12:
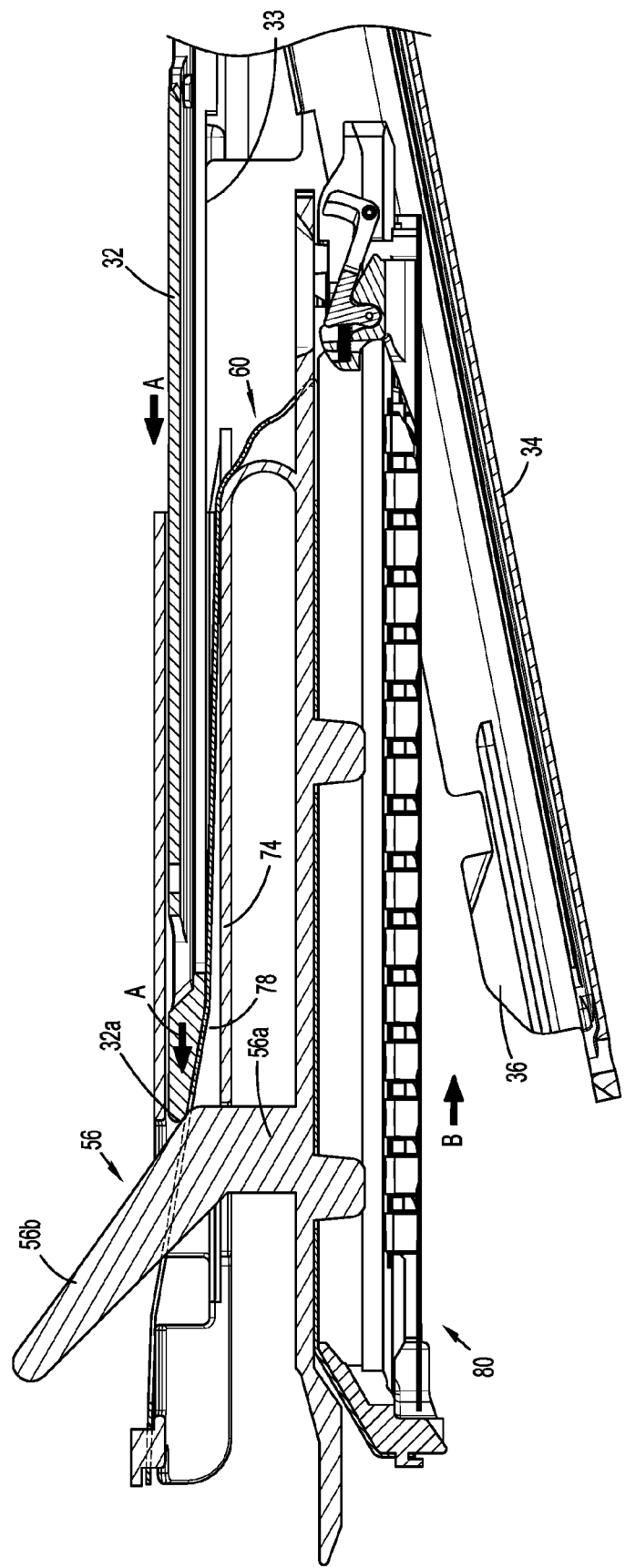
FIG. 12 is a side cross-sectional view taken along section line 12-12 of FIG. 11.
Figure 14:
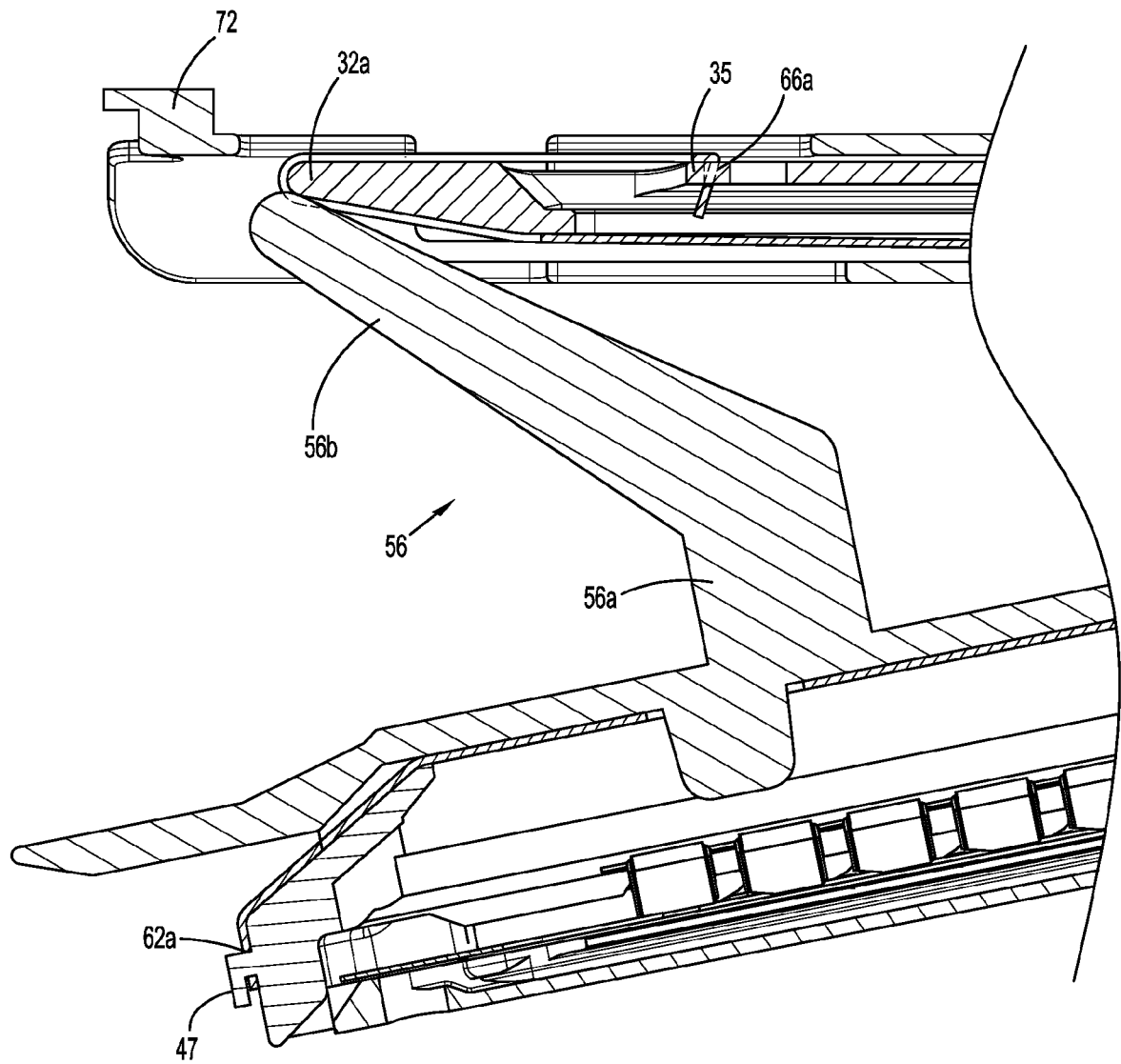
FIG. 14 is an enlarged view of a distal portion of the loading tool and an anvil showing attachment of the buttress to the anvil.
Figure 15:
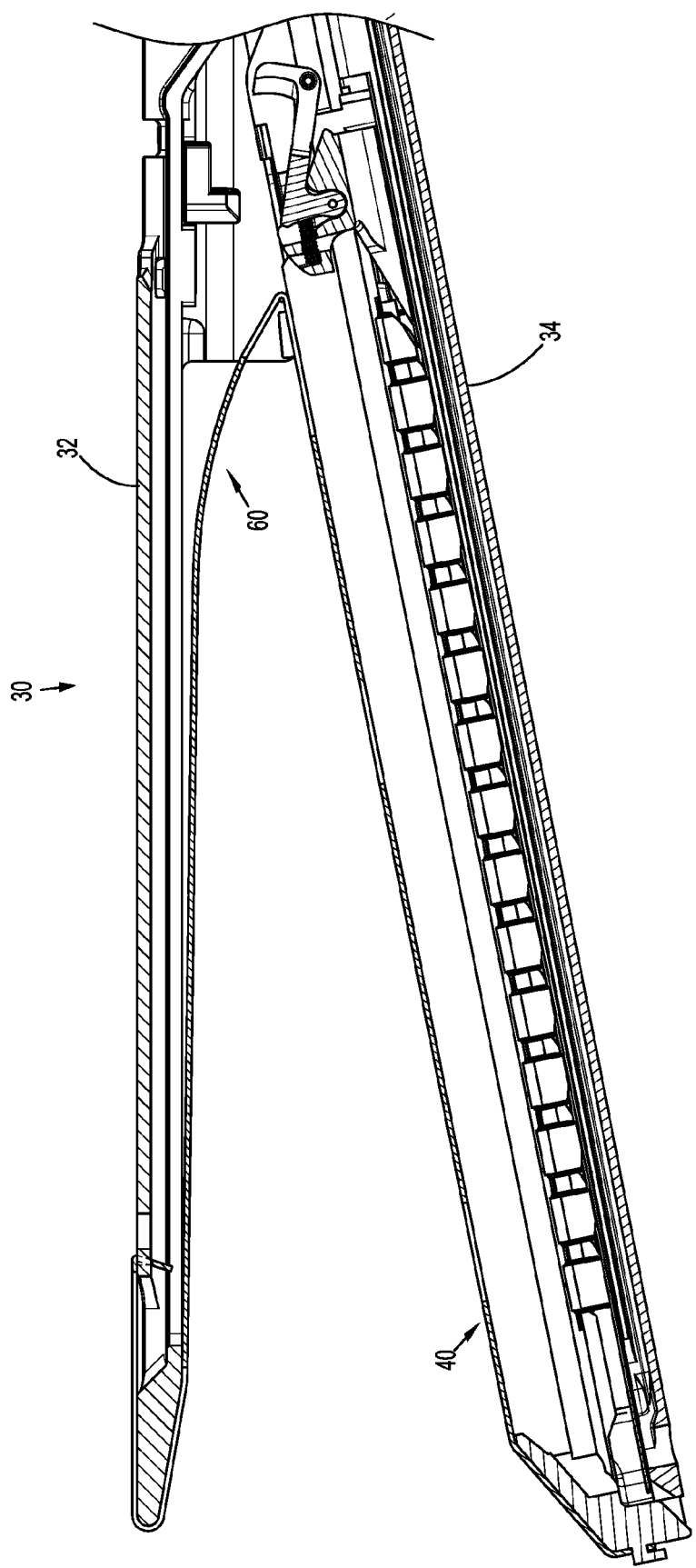
FIG. 15 is a side cross-sectional view of FIG. 12 showing the cartridge loaded into the channel, the buttress attached to the anvil, and the loading tool removed.

Referring now to FIGS. 11-15, attachment of the buttress 60 and cartridge 40 to the tool assembly 30 using the loading assembly 80 is shown. Initially, the cartridge 40 and the buttress 60 are attached to the carrier 82 forming the loading assembly 80 as described hereinabove. With the loading assembly 80 oriented at an angle with respect to the channel 36 of the second jaw member 34, a proximal end of the cartridge 40 is positioned in a proximal portion of the channel 36 of the second jaw member 34. Concurrently, the first jaw member 32 of the tool assembly 30 is slid into the passage 78 of the shell 70 as indicated by arrows "A" until a tapered, distal end 32a of the first jaw member 32 abuts the finger 56b of the arm 56 as seen in FIG. 12. Inserting the first jaw member 32 into the passage 78 of the shell 70 creates contact between the first jaw member 32 and the distal region 64 of the buttress 60 that removes some of the slack in the buttress 60 and positions the distal region 64 of the buttress 60 against the first jaw member 32. With the first jaw member 32 located in the passage 78 of the shell 70 and the cartridge 40 partially positioned in the channel 36 of the second jaw member 34 (FIG. 12), the loading assembly 80 is translated proximally relative to the first and second jaw members 32, 34 (FIG. 13) as indicated by arrow "B", thereby seating the cartridge 40 in the channel 36 of the second jaw member 34 and increasing the tension on the buttress 60. In particular, as the loading assembly 80 is translated proximally relative to the first and second jaw members 32, 34, the distal end 32a of the first jaw member 32 cams against a surface of the finger 56b. As the first and second jaw members 32, 34 are in a fixed spaced apart configuration, camming the distal end 32a of the first jaw member 32 against the finger 56b urges the platform 50 and cartridge 40 towards the channel 36 of the second jaw member 34. The hinge 79 flexibly couples the shell 70 and platform 50 and continued relative proximal movement between the carrier 82 and the first and second jaw members 32, 34 deflects the platform 50 away from the shell 70. Deflecting the platform 50 relative to the shell 70 transitions them from the initial configuration to the deployed configuration. This increases the tension on the buttress 60 and removes the remaining slack in the buttress 60. Once the cartridge 40 is seated in the channel 36 of the second jaw member 34, the tabs 41 on the cartridge 40 engage slots 37 of the channel 36. This arrangement releasably retains the cartridge 40 in the channel 36 of the second jaw member 34. With the cartridge 40 seated in the channel 36, the clinician uncouples the distal orifice 66a of the buttress 60 from the peg 72 of the shell 70 and attaches it to a hook 35 on a top surface of the first jaw member 32 as seen in FIG. 14. Now the buttress 60 is no longer connected to the carrier 82 and the carrier 82 can be separated from the tool assembly 30. This is accomplished by lifting the tab 59 on the distal end of the platform 50 thereby separating the platform 50 from the cartridge 40 and translating the carrier 82 distally relative to the tool assembly 30 leaving the cartridge 40 and buttress 60 coupled to the tool assembly 30 as shown in FIG. 15.

Referring now to FIGS. 16-19, another aspect of the presently disclosed tool assembly is shown as tool assembly 130. The tool assembly 130 may be substituted for the tool assembly 30 in the stapling instrument 10. Similar to tool assembly 30, the tool assembly 130 includes first and second jaw members 132, 134 that are pivotably coupled to one another. The first and second jaw members 132, 134 are pivotable between an open or spaced apart configuration similar to the tool assembly 30 (FIG. 4) and a closed or approximated configuration (FIG. 16). The first jaw member 132 includes an anvil 133 with staple deforming concavities (not shown) such as described in the '139 patent. The second jaw member 134 includes a generally U-shaped channel 136 (FIG. 19) that is configured to receive a cartridge 140. The cartridge 140 is releasably retained in the channel 136 due to the interaction between tabs 142 formed along the cartridge 140 and apertures 138 formed in the channel 136. Support struts 144 are formed on the cartridge 140 and are positioned to rest on sidewalls 139 of the channel 136 to further stabilize the cartridge 140 within the channel 136. The cartridge 140 includes staple pockets 146 configured to store staples 150 therein.

Figure 19:
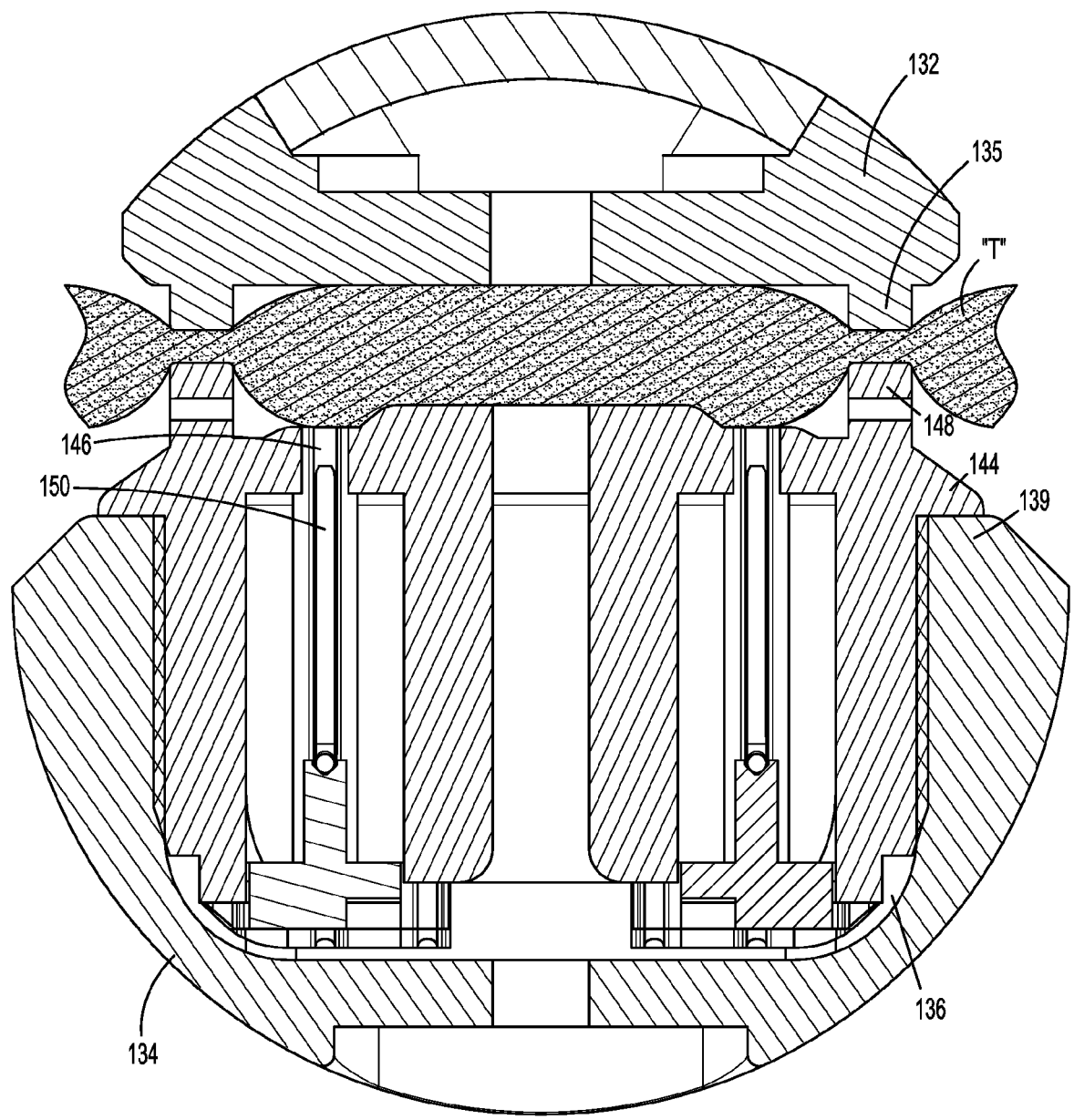
FIG. 19 is an end cross-sectional view taken along section line 19-19 of FIG. 18.

The anvil 133 of the first jaw member 132 includes knobs 135 extending from the anvil 133 towards the cartridge 140 and the cartridge 140 includes protrusions 148 extending towards the knobs 135. The knobs and protrusions 135, 148 are arranged in linear rows along the anvil 133 and cartridge 140. The knobs and protrusions 135, 148 are also laterally spaced apart as seen in FIG. 19. The knobs 135 are generally hemispherical dome-like structures extending from the anvil 133. Opposing the knobs 135 are the corresponding protrusions 148 on the cartridge 140. Each protrusion 148 has a trapezoidal shape with a void 148c defined between top and bottom portions 148a, 148b of the protrusion 148. It is contemplated that the knobs and protrusions 135, 148 are molded onto the anvil 133 and cartridge 140, respectively.

The knobs 135 are formed from a different material than the protrusions 148. In particular, the protrusions 148 are formed of a more deformable material than the knobs 135. It is contemplated that the protrusions 148 may be formed from nylon, polypropylene, or another plastic with elastomeric properties. The cartridge 140 may be formed from a material with sufficient flexibility or the specified area may be overmolded with the desired material. When the first and second jaw members 132, 134 are in the approximated configuration, there is a gap defined between the knobs and protrusions 135, 148 as seen in FIG. 17. With tissue "T" captured between the first and second jaw members 132, 134 in the approximated configuration, a downward force applied by the knobs 135 compresses tissue "T" against the protrusions 148. As the protrusions 148 are more deformable than the knobs 135, the top portions 148a of the protrusions 148 deflect under the applied force (FIG. 18). The interaction between the knobs and protrusions 135, 148 compresses tissue "T" captured between the anvil and cartridge 133, 140. The tissue compression minimizes tissue movement relative to the anvil and cartridge 133, 140 while reducing the risk of over compressing the tissue "T". The amount that the protrusions 148 deflect is proportional to the thickness of tissue "T" captured between the anvil and cartridge 133, 140. When the anvil and cartridge 133, 140 are in the approximated configuration, tissue "T" having a first thickness will result in a first amount of deflection of the protrusions 148 and tissue "T" having a second thickness that is greater than the first thickness will result in a second amount of deflection of the protrusions 148 that is greater than the first amount of deflection. The increased amount of deflection of the protrusions 148 in response to the presence of tissue "T" with a greater thickness reduces the compressive force applied to the tissue "T" captured between the anvil and cartridge 133, 140. Thus, regardless of the tissue thickness, the interaction between the knobs and protrusions 135, 148 provides a variable amount of compression that is proportional to the thickness of tissue positioned between the knobs and protrusions 135, 148 thereby reducing the risk of tissue trauma while concurrently minimizing movement of the tissue relative to the anvil and cartridge 133, 140.

While illustrated as being used in a powered surgical stapling instrument, it is contemplated, and within the scope of the present disclosure for the loading assembly and the tool assembly to be configured for use with various electromechanical and/or electrosurgical instruments and systems. For example, the loading assembly and the tool assembly may be utilized in robotic surgical systems, such as the robotic surgical system shown and described in U.S. Pat 8,828,023, the entire content of which is incorporated herein by reference.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A loading assembly for use with a surgical stapling instrument, the loading assembly comprising:
   a cartridge having a cartridge body with rows of staple pockets that are configured to retain staples therein;
   a carrier including:
      a platform adapted to releasably retain the cartridge and including an arm, and
      a shell laterally spaced from the platform and flexibly coupled thereto, the arm extending through the shell at an acute angle, the shell having a passage that is configured to receive a jaw member of the surgical stapling instrument therethrough; and
   a surgical buttress having distal and proximal regions, the distal region including a first orifice and a cutout, the proximal region including a second orifice, the first orifice attachable to a peg located in a distal region of the shell and the second orifice attachable to a post located in a distal region of the cartridge such that a portion of the surgical buttress extends through the passage of the shell, the cutout configured to receive the arm therethrough.

2. The loading assembly according to claim 1, further including a hinge that flexibly couples the shell to the platform.

3. The loading assembly according to claim 1, wherein the cartridge body includes projections extending laterally therefrom, the projections configured to releasably engage studs extending from the platform.

4. The loading assembly according to claim 1, wherein the arm extends through the cutout.

5. The loading assembly according to claim 1, wherein the cartridge is insertable into a channel of the surgical stapling instrument.

6. The loading assembly according to claim 5, wherein the cartridge is partially disposed in the channel of the surgical stapling instrument and the jaw member of the surgical stapling instrument is disposed in the passage of the shell such that a distal portion of the jaw member contacts the arm.

7. The loading assembly according to claim 6, wherein proximal movement of the carrier relative to the jaw member seats the cartridge in the channel.

8. The loading assembly according to claim 6, wherein the shell and platform are parallel to one another and proximal movement of the carrier relative to the jaw member spaces the platform away from the shell defining an acute angle therebetween.

9. The loading assembly according to claim 8, wherein the first orifice is separated from the peg of the shell and attached to a hook on the jaw member.

10. A loading assembly usable with a surgical instrument, the loading assembly comprising:
   a cartridge having a cartridge body with rows of staple pockets that are configured to retain staples therein;
   a carrier including:

a platform configured to releasably retain the cartridge, a shell laterally spaced from the platform and parallel therewith, the shell including a passage that is configured to receive a jaw member of the surgical instrument therethrough, and an arcuate hinge flexibly connecting the platform and the shell; and a surgical buttress having a first orifice in a distal region thereof and a second orifice in a proximal region thereof, the first orifice attachable to a peg located in a distal region of the shell and the second orifice attachable to a post located in a distal region of the cartridge such that a portion of the surgical buttress extends through the passage of the shell.

11. The loading assembly according to claim 10, further including an arm extending from the platform at an acute angle thereto, the arm extending through a cutout of the surgical buttress.

12. The loading assembly according to claim 11, wherein the cartridge is partially disposed in a channel of the surgical instrument and the jaw member of the surgical instrument is disposed in the passage of the shell such that a distal portion of the jaw member contacts the arm.

13. The loading assembly according to claim 12, wherein proximal movement of the carrier relative to the jaw member seats the cartridge in the channel.

14. The loading assembly according to claim 12, wherein proximal movement of the carrier relative to the jaw member spaces the platform away from the shell defining an acute angle therebetween.

15. The loading assembly according to claim 14, wherein the first orifice is separated from the peg of the shell and attached to a hook on the jaw member.

16. The loading assembly according to claim 10, wherein the platform includes a keel configured to engage a slot of the cartridge and opposed shoulders configured to engage opposed sidewalls of the cartridge thereby aligning the cartridge and the carrier.

* * * * *